United States Patent
Long et al.

(10) Patent No.: US 9,422,335 B2
(45) Date of Patent: Aug. 23, 2016

(54) MODIFIED TOLL-LIKE RECEPTOR 2 (TLR2) LIGANDS AS INHIBITORS OF NEUTROPHIL RECRUITMENT

(75) Inventors: Elizabeth M. Long, Calgary (CA); Stephen M. Robbins, Calgary (CA); Paul Kubes, Calgary (CA); Ela Kolaczkowska, Calgary (CA)

(73) Assignee: UTI Limited Partnership, Calgary, AB ( * ) Notice: Subject to any disclaimer, the term of this patent is extended or adjusted under 35 U.S.C. 154(b) by 80 days.

(21) Appl. No.: 14/241,484

(22) PCT Filed: Aug. 30, 2012

(86) PCT No.: PCT/IB2012/002208
§ 371 (c)(1),
(2), (4) Date: Nov. 17, 2014

(87) PCT Pub. No.: WO2013/030678
PCT Pub. Date: Mar. 7, 2013

(65) Prior Publication Data
US 2015/0065414 A1    Mar. 5, 2015

Related U.S. Application Data

(60) Provisional application No. 61/529,044, filed on Aug. 30, 2011.

(51) Int. Cl.
*C07K 7/08* (2006.01)
*A61K 45/06* (2006.01)
*A61K 38/10* (2006.01)
*C07K 14/31* (2006.01)

(52) U.S. Cl.
CPC . *C07K 7/08* (2013.01); *A61K 38/10* (2013.01); *A61K 45/06* (2013.01); *C07K 14/31* (2013.01)

(58) Field of Classification Search
CPC .......... A61K 2300/00; A61K 31/202; A61K 31/201; A61K 9/2013; A61K 38/00; A61K 38/10; A61K 9/0019
See application file for complete search history.

(56) References Cited

U.S. PATENT DOCUMENTS

2006/0014820 A1* 1/2006 Burstein ............. A61K 31/202
                                                             514/423
2007/0232579 A1* 10/2007 Freeman ............ A61K 31/21
                                                             514/178

OTHER PUBLICATIONS

Fujitani et al. Structural transition of a 15 amino acid residue peptide induced by GM1. Carbohydr Res. Sep. 3, 2007;342(12-13):1895-903.*

Shibata et al. The N-Terminal Lipopeptide of a 44-kDa Human Gingival Fibroblasts Molecule-1 on the Cell Surface of Normal Expression of Intercellular Adhesion Membrane-Bound Lipoprotein of Mycoplasma salivarium Is Responsible for the Expression of Intercellular Adhesion Molecule-1 on the Cell Surface of Normal Human Gingival Fibroblasts. J Immunol.*

Tokeda et al. Recognition of lipopeptides by Toll-like receptors. J Endotoxin Res. 2002;8(6):459-63.*

(Continued)

*Primary Examiner* — Satyanarayana R Gudibande
*Assistant Examiner* — Jia-Hai Lee
(74) *Attorney, Agent, or Firm* — Parker Highlander PLLC

(57) ABSTRACT

The present invention provides modified TLR2 ligands useful for modulating inflammatory responses. In particular, the ligands comprise (a) a fatty acid di- or tri-linoleate and (b) a GM1-binding peptide. The linoleate provides the anti-inflammatory function, while the GM1-binding peptide facilitates endocytosis.

17 Claims, 21 Drawing Sheets

(56) References Cited

OTHER PUBLICATIONS

Triantafilou et al. Lipoteichoic acid and toll-like receptor 2 internalization and targeting to the Golgi are lipid raft-dependent. J Biol Chem. Sep. 24, 2004;279(39):40882-9.*

Montaner et al. Ganglioside GM1-binding peptides as adjuvants of antigens inoculated by the intranasal route. Vaccine 24 (2006) 1889-1896.*

Behr et al., "The structure of pneumococcal lipoteichoic acid. Improved preparation, chemical and mass spectrometric studies," *European Journal of Biochemistry*, 207(3):1063-1075, 1992.

Hirata et al., "Selective synergy in anti-inflammatory cytokine production upon cooperated signaling via TLR4 and TLR2 in murine conventional dendritic cells," *Molecular Immunology*, 45(10):2734-2742, 2008.

Liang et al., "Characterization of sparstolonin B, a Chinese herb-derived compound, as a selective Toll-like receptor antagonist with potent anti-inflammatory properties," *Journal of Biological Chemistry*, 286(30):26470-26479, 2011.

Long et al., "A subclass of acylated anti-inflammatory mediators usurp Toll-like receptor 2 to inhibit neutrophil recruitment through peroxisome proliferator-activated receptor gamma," *PNAS*, 108(39):16357-16362, 2011.

Long et al., "Lipoteichoic acid induces unique inflammatory responses when compared to other toll-like receptor 2 ligands," *PloS One*, 4:e5601, 2009.

Manicassamy et al., "Modulation of adaptive immunity with Toll-like receptors," *Seminars in Immunology*, 21(4):185-193, 2009.

PCT International Search Report and Written Opinion issued in International Patent Application No. PCT/IB2012/002208, dated May 27, 2013.

Schroder et al., "Lipoteichoic acid (LTA) of *Streptococcus pneumoniae* and *Staphylococcus aureus* activates immune cells via Toll-like receptor (TLR)-2, lipopolysaccharide-binding protein (LBP), and CD14, whereas TLR-4 and MD-2 are not involved," *J. Biol. Chem.*, 278(18):15587-15594, 2003.

Serhan et al., "Resolving inflammation: dual anti-inflammatory and pro-resolution lipid mediators," *Nature Reviews. Immunology*, 8(5):349-361, 2008.

Straus and Glass, "Anti-inflammatory actions of PPAR ligands: new insights on cellular and molecular mechanisms," *Trends Immunol.*, 28(12):551-558, 2007.

Villacorta et al., "PPARgamma and its ligands: therapeutic implications in cardiovascular disease," *Clinical Science*, 116(3):2058-218, 2009.

Yipp et al., "Profound differences in leukocyte-endothelial cell responses to lipopolysaccharide versus lipoteichoic acid," *J. Immunol.*, 168(9):4650-4658, 2002.

* cited by examiner

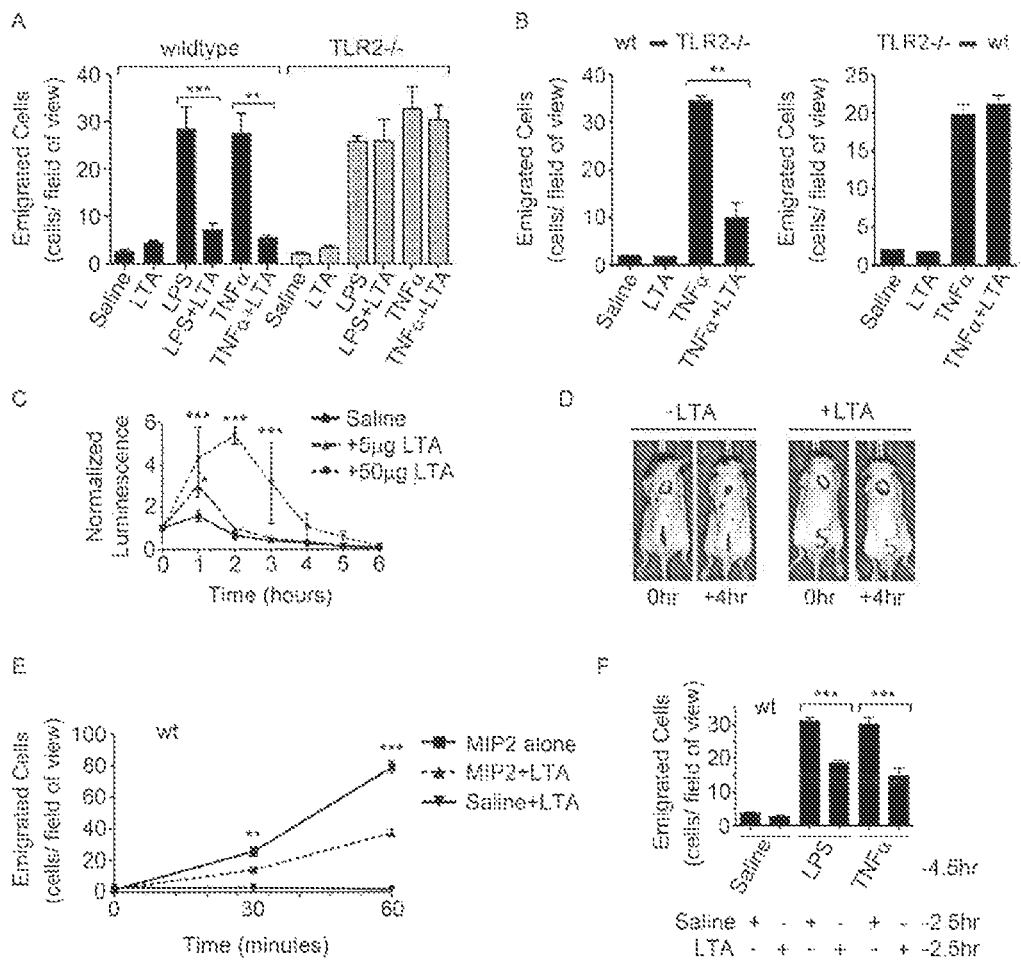
FIG. 1A-F

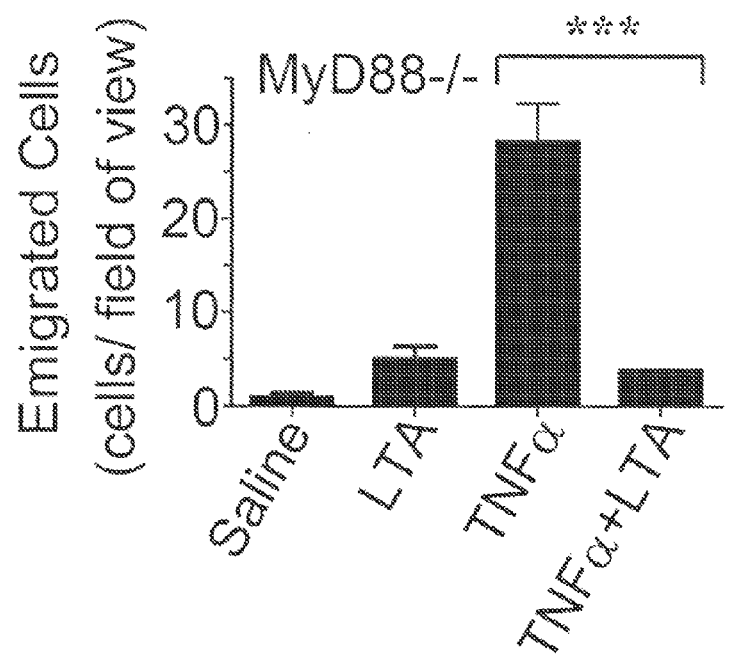
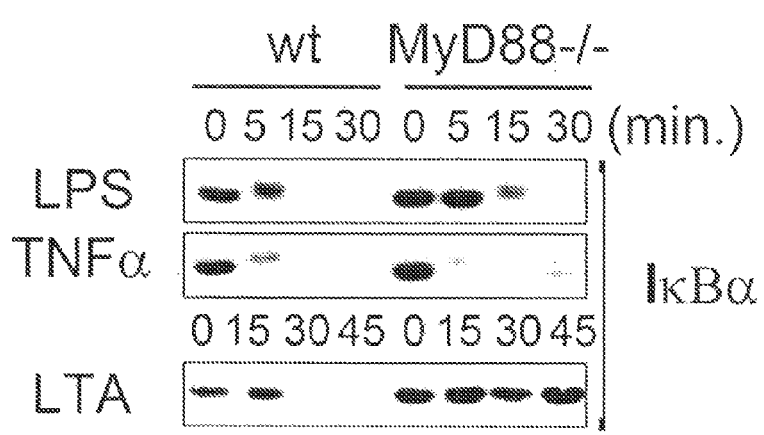
FIG. 2A-B

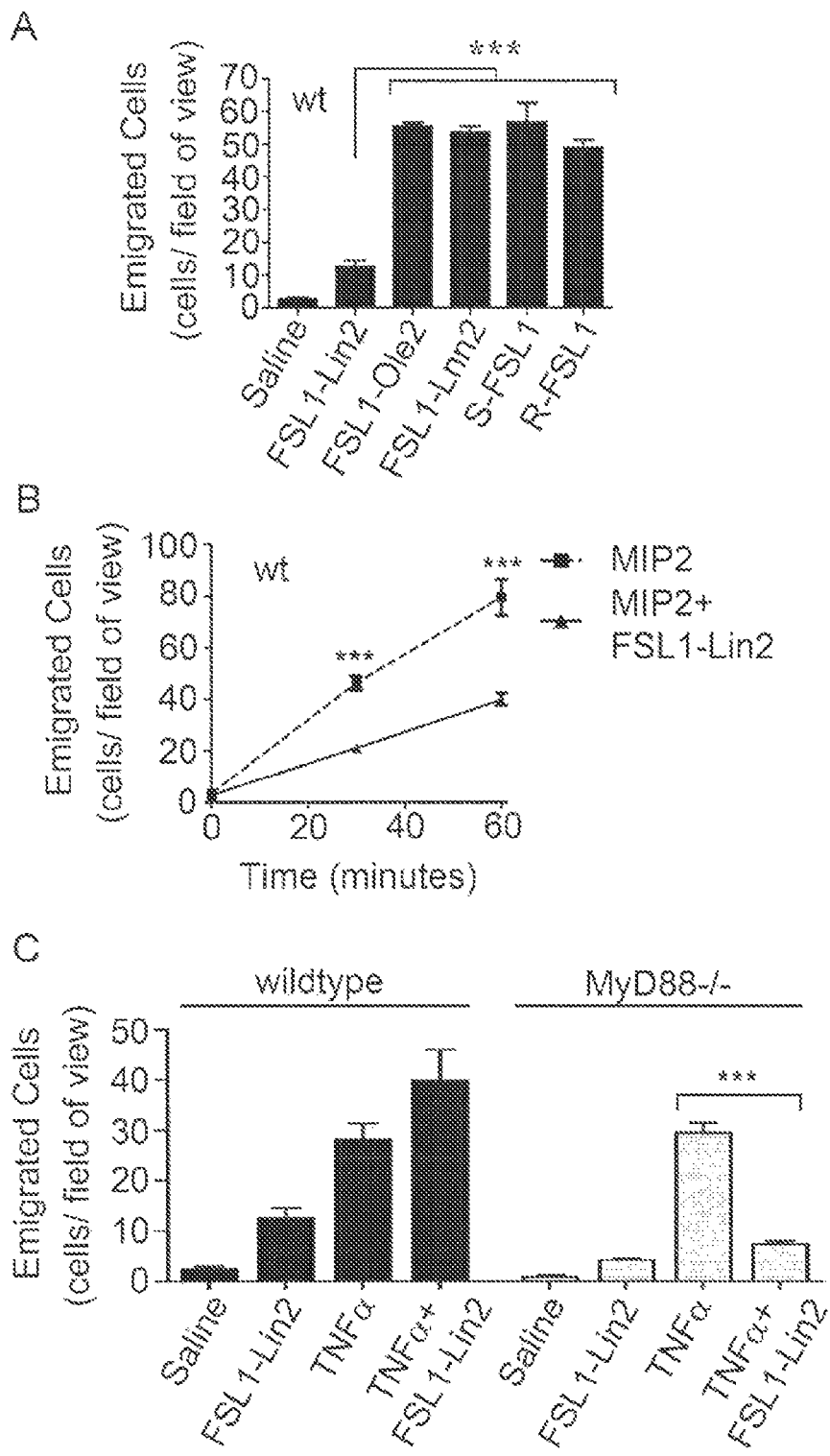
FIG. 3A-C

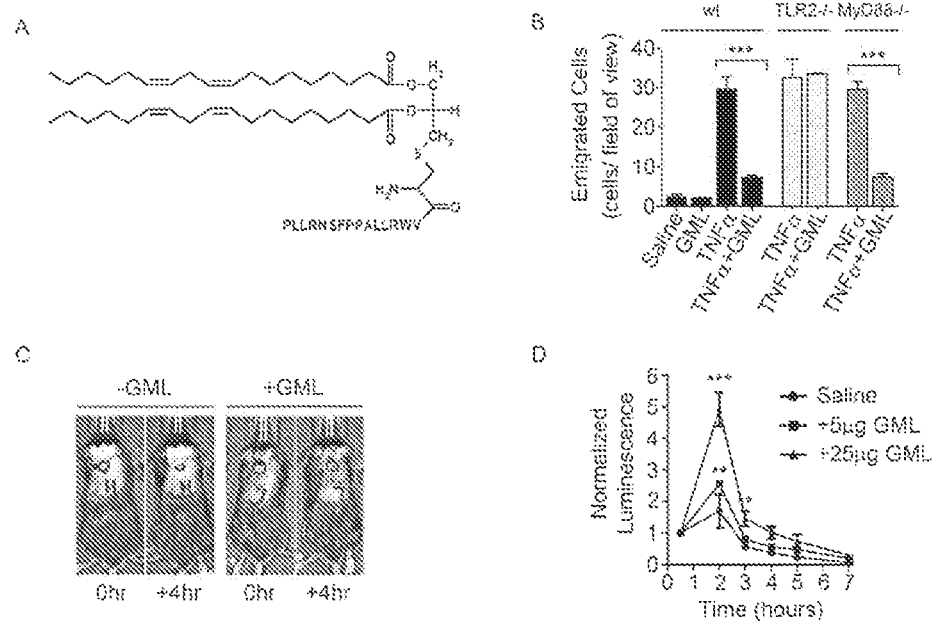
FIG. 4A-D

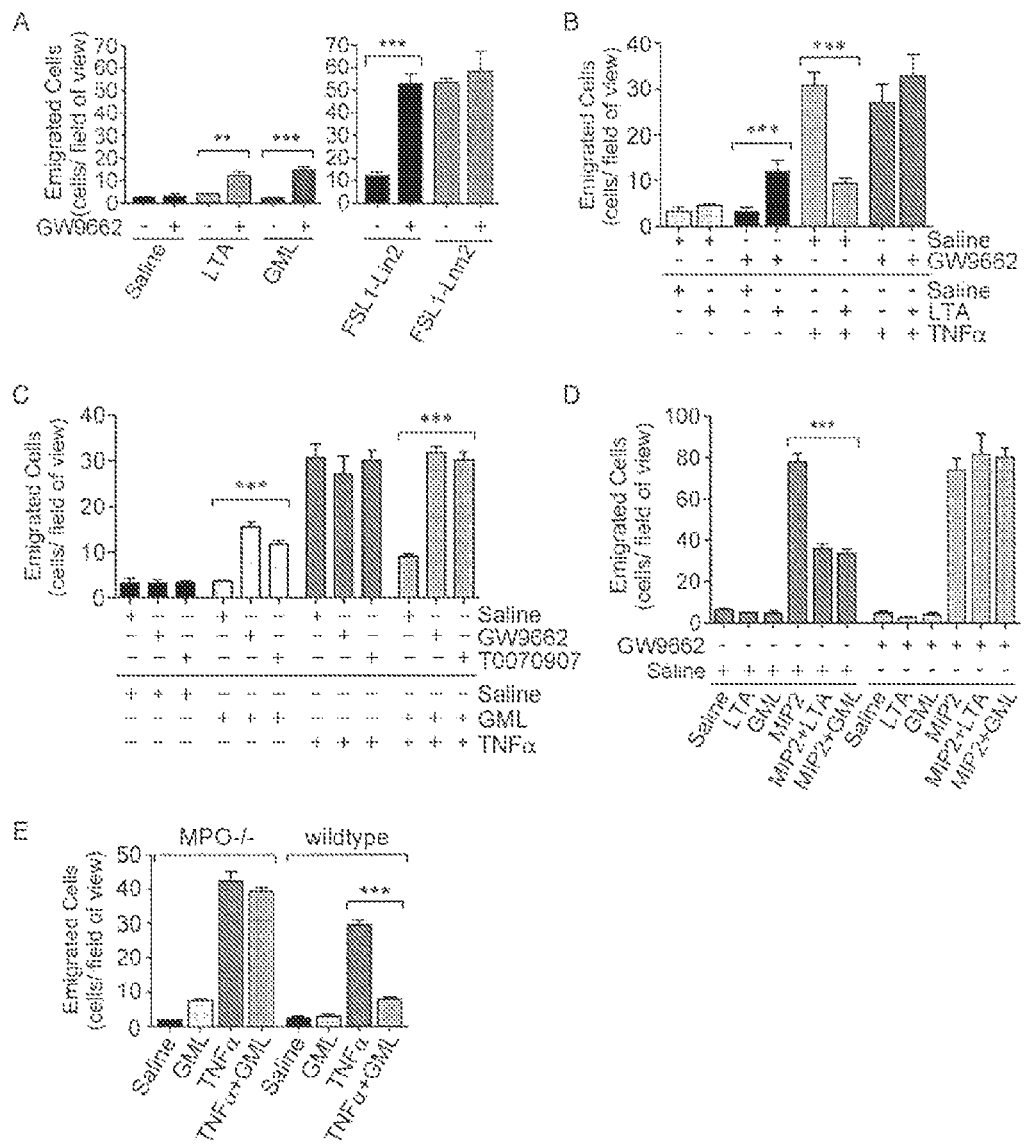
FIG. 5A-E

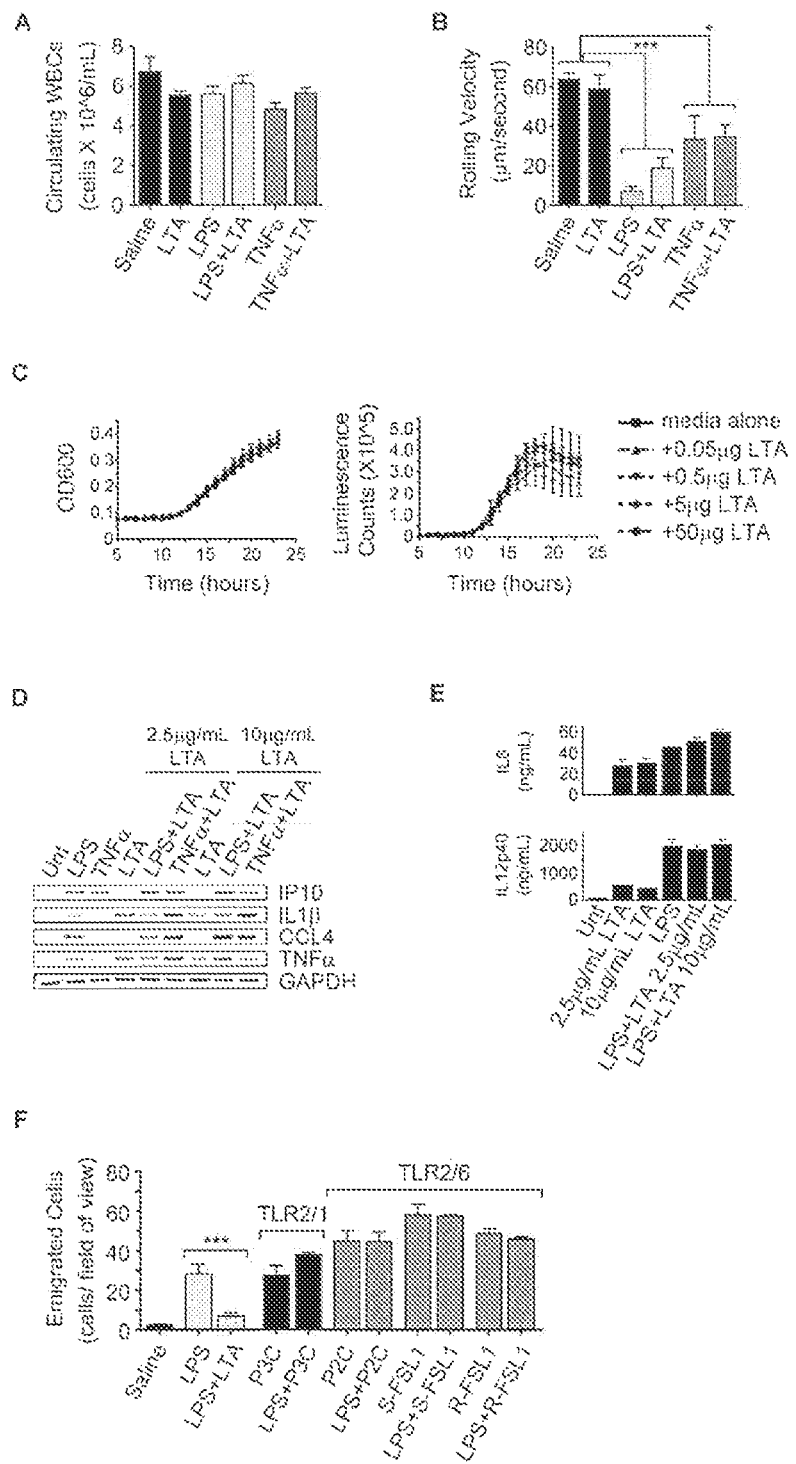
FIG. 6A-F

| Ligand Name | Lipopeptide Sequence | Acyl Chain Composition | Acyl Chain Structure |
|---|---|---|---|
| FSL-1 | Pam2-CysGDPKHPKSF | di-palmitate | |
| FSL1-Lin2 | Lin2-CysGDPKHPKSF | di-linoleate | |
| FSL1-Ole2 | Ole2-CysGDPKHPKSF | di-oleate | |
| FSL1-Lnn2 | Lnn2-CysGDPKHPKSF | di-linolenate | |

FIG. 11

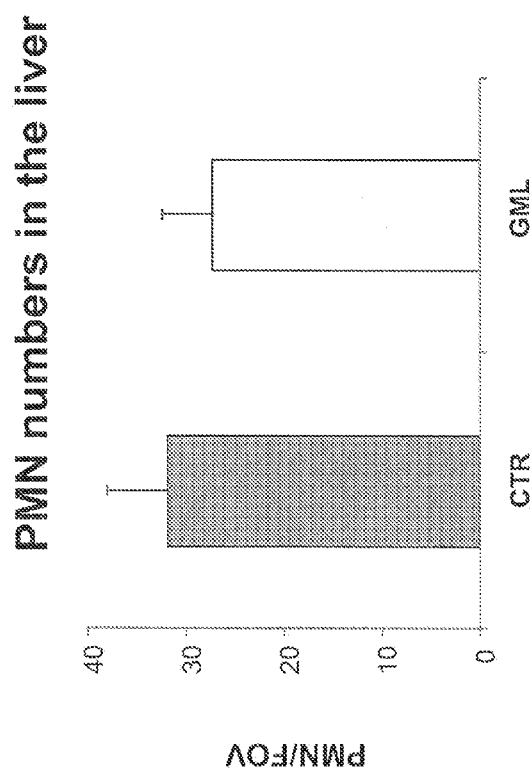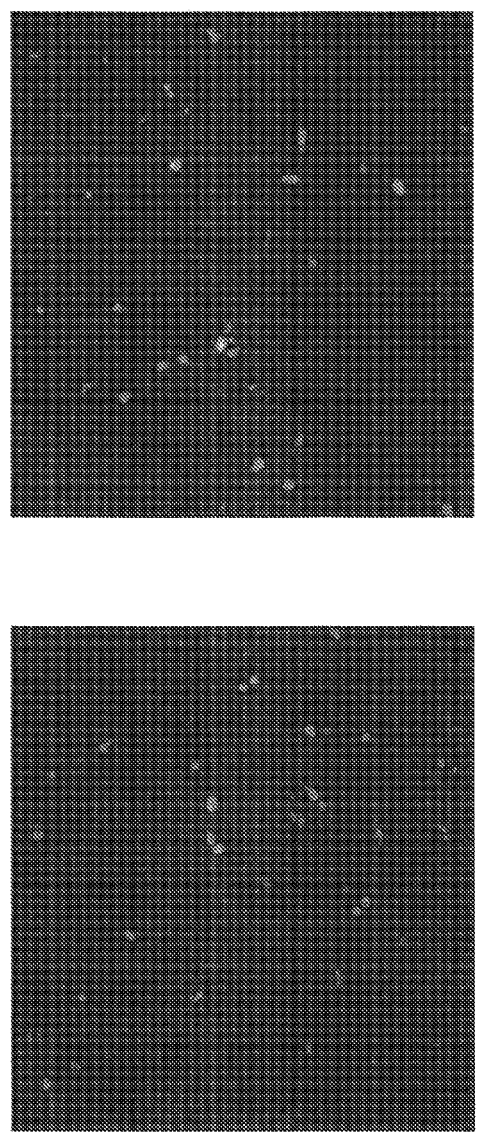
FIG. 17

FIG. 18
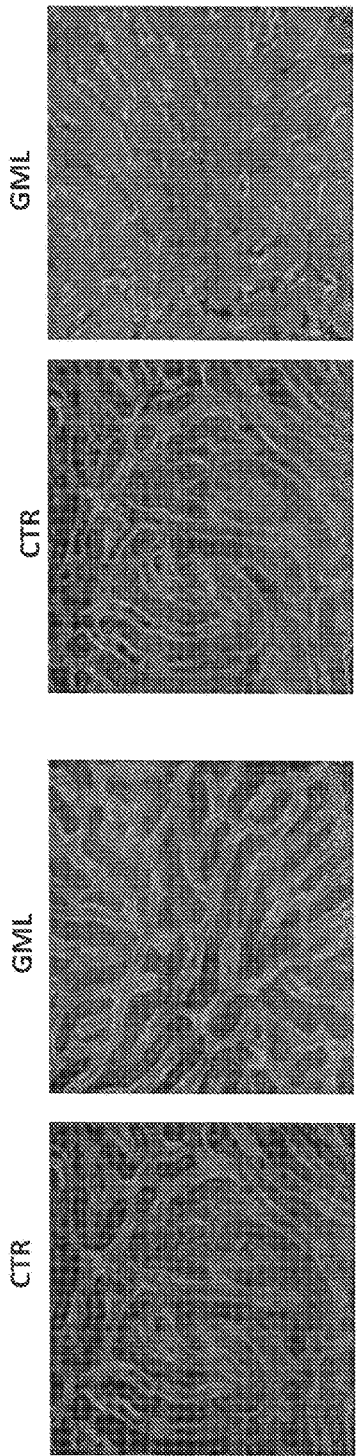
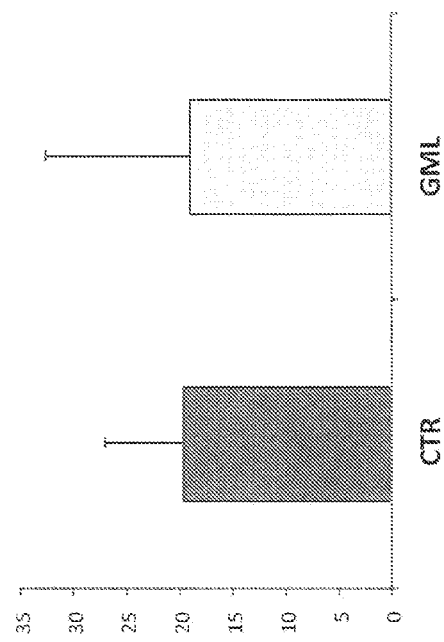
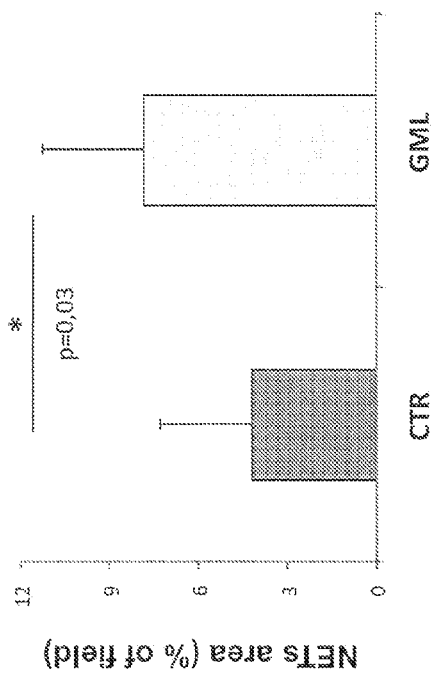

Effects of GML on S. aureus systemic infection

| | After GML treatment |
|---|---|
| WBC numbers | higher |
| PMN numbers in the lung | unchanged |
| PMN numbers in the liver | unchanged |
| Damage to the liver (abscess area) | lower |
| Damage to the liver ALT | lower |
| CFUs in the liver (and the lung) | less (none) |
| NETs in the liver: | |
| NE | more |
| histones | unchanged |

FIG. 19

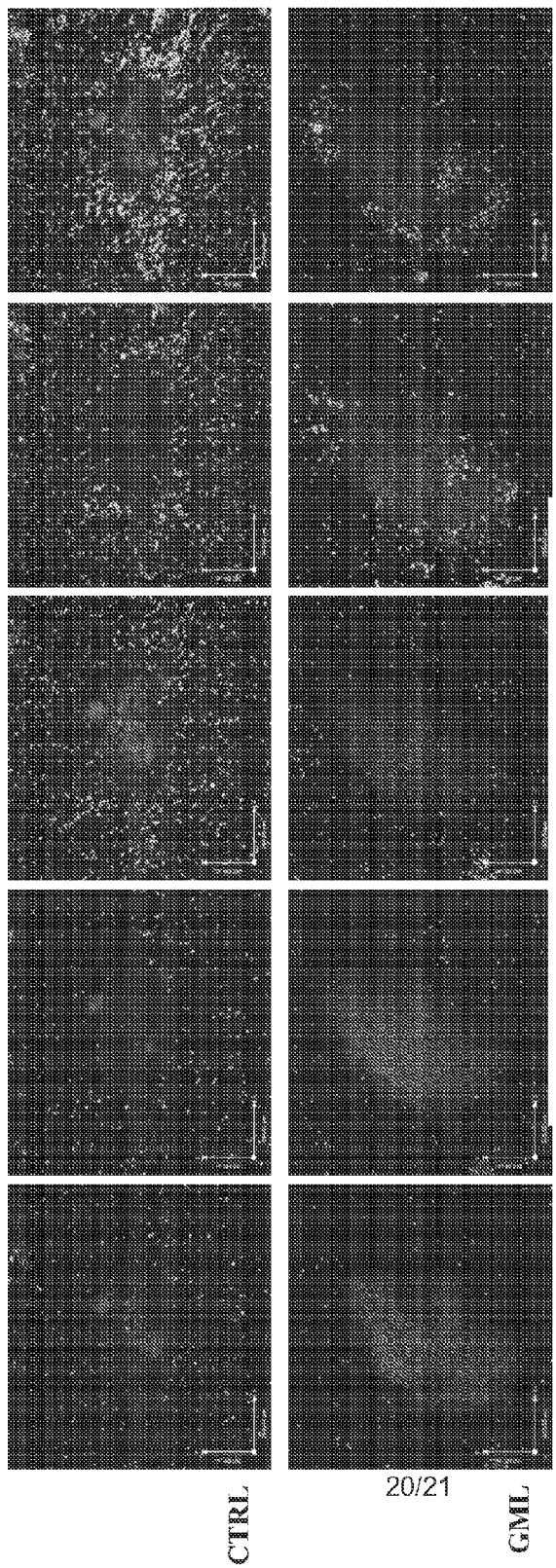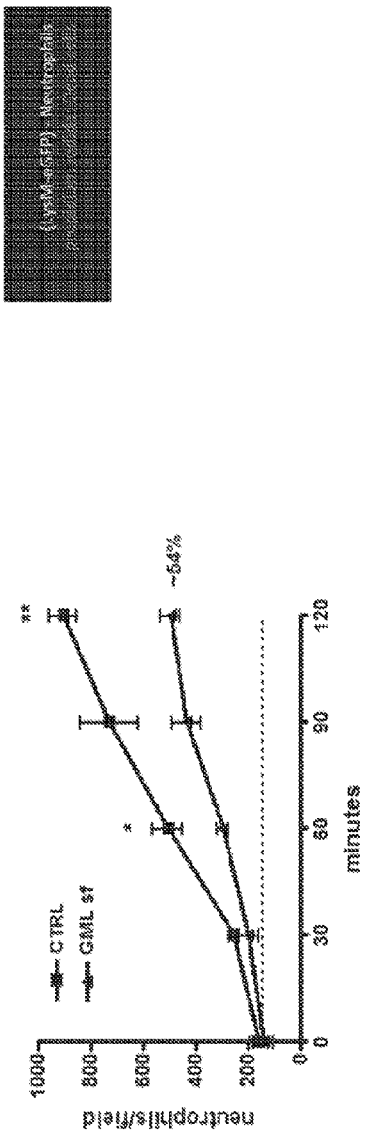
FIG. 20

MODIFIED TOLL-LIKE RECEPTOR 2 (TLR2) LIGANDS AS INHIBITORS OF NEUTROPHIL RECRUITMENT

This application is a national phase application under 35 U.S.C. §371 of International application No. PCT/IB2012/002208, filed Aug. 30, 2012, which claims benefit of priority to U.S. Provisional Application Ser. No. 61/529,044, filed Aug. 30, 2011. The entire contents of each of the above referenced disclosures are specifically incorporated herein by reference.

The sequence listing that is contained in the file named "UNTIP0122US_ST25.txt", which is 2 KB (as measured in Microsoft Windows®) and was created on Feb. 26, 2014, is filed herewith by electronic submission and is incorporated by reference herein.

BACKGROUND OF THE INVENTION

1. Field of the Invention

The present invention relates generally to the fields of cell biology, pathology and intracellular signaling. More particularly, it concerns methods and compositions relating to modified Toll-like receptor 2 ligands that inhibit inflammation to a broad array of pro-inflammatory stimuli by usurping TLR2 and activating peroxisome proliferator-activated receptors.

2. Description of Related Art

Toll-like receptors (TLRs) are important sentinel receptors of the immune system. Upon ligand binding, these receptors initiate receptor-specific recruitment of a family of TIR-domain-containing adaptor proteins, which further initiate signaling cascades that culminate in the activation of cell-type-specific, and receptor/ligand-specific inflammatory responses (Brikos and O'Neill, 2008; Beutler, 2009; Manicassamy and Pulendran, 2009). In particular, TLR2 forms heterodimers with either TLR1 or 6 in order to initiate inflammatory responses upon stimulation with a wide variety of microbial-derived ligands (Ozinsky et al., 2000; Zahringer et al., 2008). A unifying feature of many of these TLR2 ligands is their acylation status, where acylation patterns impart specificity to receptor-ligand interactions; di-acylated ligands are recognized by TLR2/6 heterodimers and tri-acylated ligands are recognized by TLR2/1 heterodimers (Kang et al., 2009; Jin et al., 2007). Principal among these ligands are acylated lipopeptides derived from bacteria, however other acylated bacterial components, such as the gram-positive bacterial cell wall component lipoteichoic acid (LTA), are also recognized by TLR2 (Schroder et al., 2003).

TLR-induced activation of acute inflammatory responses is ultimately responsible for the eradication of infectious agents, in part through the recruitment of polymorphonuclear neutrophils from the bloodstream into the affected tissue. This recruitment follows a well-characterized cascade of successive steps, reviewed in refs (Ley et al., 2007; Petri et al., 2008) that allow the neutrophils to deal with the offending microbes through the activities of proteases, bactericidal peptides and reactive intermediates. In addition to the host-protective role that these cells play in the immune response, excessive or inappropriate neutrophil recruitment results in significant pathophysiology and morbidity (Jaeschke and Hasegawa, 2006; Zemans et al., 2009; Brown and Mayer, 2007).

SUMMARY OF THE INVENTION

Thus, in accordance with the present invention, there is provided a method of inhibiting pro-inflammatory signaling in a subject in need thereof comprising administering to said subject a modified TLR2 ligand comprising (a) a fatty acid di- or tri-linoleate and (b) a GM1-binding peptide. The GM1-binding peptide may comprise the sequence VWRLLAPPFSNRLLP (SEQ ID NO: 1), WRLLAPPFSNRLLP (SEQ ID NO: 2) or (W/F)RXL(X/P)(P/X)XFXX(R/X)(X/R)XP (SEQ ID NO: 3), where X can be any amino acid. The di- or tri-linoleate may be a peroxisome proliferation activated receptor (PPAR) ligand.

The subject may be a human, or non-human mammal. The subject may suffer from chronic inflammation, such as that comprising leukyocyte recruitment. The condition may be inflammatory bowel disease (including ulcerative colitis and Crohns), arthritis, psoriasis, respiratory neutrophila, chronic tissue injury. The subject may suffer from acute inflammation, such as from tissue trauma (including fractures sprains, burns, surgery), sepsis, methicillin-resistant *Staphylococcus* infection, sterile injury (tissue injury wounding), acute inflammatory tissue (e.g., liver), injury respiratory neutrophilia, acute neutrophilic dermatosis, and during organ/tissue transplantation.

The TLR2 ligand may be is administered subcutaneously, topically, intravenously, suppository, or via a shunt. The method may further comprise administering to said subject a second anti-inflammatory therapy, such as an NSAID, a steroid, an anti-adhesion molecule therapy, a COX inhibitor, an immunomodulator (e.g., anti-TNF based therapy), an anti-histamine, an antibiotic or an anti-viral.

In another embodiment, there is provided a method of inhibiting leukocyte recruitment to an inflammatory site in a subject in need thereof comprising administering to said subject a modified TLR2 ligand comprising (a) a fatty acid di- or tri-linoleate and (b) a GM1-binding peptide. The GM1-binding peptide may comprise the sequence VWRLLAPPFSNRLLP (SEQ ID NO: 1), WRLLAPPFSNRLLP (SEQ ID NO: 2) or (W/F)RXL(X/P)(P/X)XFXX(R/X)(X/R)XP (SEQ ID NO: 3), where X can be any amino acid. The di- or tri-linoleate may be a peroxisome proliferation activated receptor (PPAR) ligand.

The subject may be a human, or non-human mammal. The subject may suffer from chronic inflammation, such as that comprising leukyocyte recruitment. The condition may be inflammatory bowel disease (including ulcerative colitis and Crohns), arthritis, psoriasis, respiratory neutrophila, chronic tissue injury. The subject may suffer from acute inflammation, such as from tissue trauma (including fractures sprains, burns, surgery), sepsis, methicillin-resistant *Staphylococcus* infection, sterile injury (tissue injury wounding), acute inflammatory tissue (e.g., liver), injury respiratory neutrophilia, acute neutrophilic dermatosis, and during organ/tissue transplantation.

The TLR2 ligand may be is administered subcutaneously, topically, intravenously, suppository, or via a shunt. The method may further comprise administering to said subject a second anti-inflammatory therapy, such as an NSAID, a steroid, an anti-adhesion molecule therapy, a COX inhibitor, an immunomodulator (e.g., anti-TNF based therapy), an anti-histamine, an antibiotic or an anti-viral. The leukyocyte recruitment to a site may be reduced 10%, 20%, 30%, 40%, 50%, 60% or 75% as compared to untreated control.

In yet another embodiment, there is provided a modified lipopeptide TLR2 ligand comprising (a) a fatty acid di- or tri-linoleate and (b) a GM1-binding peptide. The GM1-binding peptide may comprise the sequence VWRLLAPPFSNRLLP (SEQ ID NO: 1), WRLLAPPFSNRLLP (SEQ ID NO: 2) or (W/F)RXL(X/P)(P/X)XFXX(R/X)(X/R)XP (SEQ ID NO: 3), where X can be any amino acid. The lipopeptide may be selected from FSL-Lnn2 and GML. The fatty acid di- or tri-linoleate may activate PPARγ.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-F. *S. aureus* LTA inhibits the in vivo acute inflammatory responses to a wide array of inflammatory stimuli, in a TLR2-dependent manner. (FIG. 1A) Wild-type and TLR2−/− male mice were given intrascrotal injections of 150 μl saline or saline containing LTA (5 ng/g), LPS (10 ng/g), TNFα (20 ng/g), either alone or in combination as indicated. Neutrophil emigration into the cremaster tissue was monitored using intravital microscopy, 4.5 hr following intrascrotal injection of the above ligands as indicated. (FIG. 1B) Bone marrow chimeric mice were given intrascrotal injections of 150 μl saline or saline containing LTA (5 ng/g) or TNFα (20 ng/g), either alone or in combination as indicated. Neutrophil emigration 4.5 hr following intrascrotal injection of the above ligands is shown. (FIGS. 1C-D) Male C57BL/6 mice were given a dorsal subcutaneous inoculum of live luminescent *E. coli* in the presence or absence of LTA; (FIG. 1C) Luminescence normalized to the detected luminescence at the time of inoculation, observed over 6 hr. (FIG. 1D) Image of two examples of these mice, (+/− LTA), taken at the time of inoculation and 4 hr later. (FIG. 1E) Neutrophil emigration into the cremaster tissue monitored by intravital microscopy following exteriorization of the cremaster and superfusion with buffer containing MIP2 (2.5 μM), MIP2 (2.5 μM)+LTA (200 ng/mL), or LTA (200 ng/mL) alone. (FIG. 1F) Intravital microscopic evaluation of the number of neutrophils that had emigrated into the cremaster tissue, 4.5 hr following an intrascrotal injection of LPS (10 ng/g) or TNFα (20 ng/g) and 2.5 hr following an intrascrotal injection of LTA (100 ng/g).

FIGS. 2A-B. The inhibitory capacity of LTA is independent of conventional TLR2 signaling pathways. (FIG. 2A) MyD88−/− mice were given an intrascrotal injection of 150 μl saline, or saline containing LTA (5 ng/g) and/or TNFα (20 ng/g), either alone or in combination as indicated, and evaluated 4.5 hr later by intravital microscopy for the number of emigrated cells within the cremaster tissue. (FIG. 2B) Wild-type or MyD88−/− bone marrow-derived macrophages were treated in vitro with LPS (100 ng/mL), TNFα (20 ng/mL), or LTA (1 μg/mL) for the indicated times, and cell lysates were subjected to Western blotting for IκBα.

FIGS. 3A-C. Molecular modification of a pro-inflammatory TLR2 ligand to contain linoleate yields a TLR2 ligand with diminished inflammatory potential and inhibitory characteristics. Mice were evaluated using intravital microscopy for the number of neutrophils emigrated into the cremaster tissue; (FIG. 3A) 4.5 hr following intrascrotal injections of 150 μl saline, or saline containing the different acyl chain-modified ligands, FSL1-Lin2, FSL1-Ole2, or FSL1-Lnn2 (all at 5 ng/g) in comparison to the parent (R/S)FSL-1 ligands, (FIG. 3B) during superfusion of the exposed cremaster with buffer containing MIP2 (2.5 μM) or MIP2 (2.5 μM)+FSL1-Lin2 (200 ng/mL), and (FIG. 3C) in wild-type mice or MyD88−/− mice 4.5 hr following intrascrotal injections of 150 μl saline, or saline containing FSL1-Lin2 (5 ng/g) and/or TNFα (20 ng/g) as indicated.

FIGS. 4A-D. Engineering of the inhibitory TLR2 lipopeptide ligand—GM1-targeted, linoleate-containing TLR2 ligand (GML). (FIG. 4A) Schematic of GML. (FIG. 4B) Wild-type, TLR2−/−, or MyD88−/− mice treated with an intrascrotal injection of 150 μl saline alone or saline containing the indicated ligands (GML 37.5 ng/g and/or TNFα 20 ng/g) either alone or in combination, and evaluated 4.5 hours later for the number of emigrated neutrophils within the cremaster tissue. (FIG. 4C-D) Male C57BL/6 mice were given a dorsal subcutaneous inoculum of live luminescent *E. coli* in the presence or absence of GML; (FIG. 4C) Image of two examples of these mice, (+/− GML), taken at the time of inoculation and 4 hr later, (FIG. 4D) Luminescence normalized to the detected luminescence at the time of inoculation, observed over 6 hr.

FIGS. 5A-E. The inhibitory capacity of TLR2 ligands requires functional signaling through PPAR. (FIGS. 5A-D) Mice were evaluated using intravital microscopy for the number of neutrophils emigrated into the cremaster tissue following intrascrotal injections of 150 μl saline alone or saline containing GW9662 (0.5 μg) or T0070907 (0.5 μg), as a 1.5 hr pre-treatment; (FIG. 5A) followed by an intrascrotal injection of 150 μl saline alone or saline containing LTA, GML, FSL1-Lin2, or FSL1-Lnn2 (each at 5 ng/g) for 4.5 hr or (FIG. 5B) followed by an intrascrotal injection of 150 μl saline alone or saline containing TNFα (20 ng/g) or TNFα (20 ng/g)+LTA (5 ng/g) for 4.5 hr or (FIG. 5C) followed by an intrascrotal injection of 150 μl saline alone or saline containing TNFα (20 ng/g) or TNFα (20 ng/g)+GML (37.5 ng/g) for 4.5 hr or (FIG. 5D) Followed by the exteriorization of the cremaster and superfusion of MIP2 (5 μM) in the presence or absence of LTA (5 μg/mL) or GML (5 μg/mL) for 60 min, (FIG. 5E) MPO−/− mice evaluated using intravital microscopy for the number of neutrophils emigrated into the cremaster tissue following intrascrotal injections of 150 μl saline containing GML (37.5 ng/g), TNFα (20 ng/g), or TNFα+GML.

FIGS. 6A-F. The inhibitory capacity of LTA preparations evaluated in vivo and in vitro. (FIG. 6A) Wild-type mice were given intrascrotal injections of 150 μl of saline, or saline containing LTA (5 ng/g), LPS (10 ng/g), or TNFα (20 ng/g) in the indicated combinations, 4.5 hrs following these injections the total number of circulating leukocytes were determined from whole blood. (FIG. 6B) The velocity of the rolling cells within the cremaster tissue was determined via intravital microscopy 4.5 hrs following intrascrotal injections of 150 μl saline containing LTA (5 ng/g), LPS (10 ng/g), or TNFα (20 ng/g) in the indicated combinations. (FIG. 6C) Luminescent *E. coli* were grown in culture in the presence of increasing amounts of LTA and monitored for any differences in growth kinetics or luminescence as a result of the presence of LTA. (FIGS. 6D-E) Bone marrow-derived macrophages were treated with either LPS (100 ng/mL) or TNFα (20 ng/mL) in the presence or absence of LTA as indicated; (FIG. 6D) mRNA isolated from these cells was used in RT-PCR reactions to determine mRNA transcript amounts for IP10, IL1β, CCL4, TNFα, and as a loading control GAPDH, (FIG. 6E) supernatants taken from these cells were used to detect secreted IL6 and IL12p40 by ELISA. (FIG. 6F) Intravital microscopy was used to evaluate emigrated neutrophils 4.5 hours following an intrascrotal injection of 150 μl of saline, or saline containing LPS (10 ng/g), or LPS plus LTA, Pam3CSK3, Pam2CSK4, S-FSL1 or R-FSL1 (each at 5 ng/g).

(FIG. 8A) Wild-type mice were given intrascrotal injections of 150 μl saline, containing FSL1-Lin2, FSL1-Ole2, FSL1-Lnn2, R-FSL1, or S-FSL1, (all at 5 ng/g), as indicated, and 4.5 hrs later the number of circulating leukocytes was determined from whole blood. (FIG. 8B) Raw264.7 cells were treated with FSL1, FSL1-Lin2, FSL1-Lnn2 or FSL1-Ole2 (all at 100 ng/mL) for the indicated times and lysates were then subjected to Western blotting for IκBα. (FIG. 8C) The number of emigrated cells was determined using intravital microscopy 4.5 hrs following intrascrotal injections containing FSL1-Lin2 (5 ng/g) into TLR2-/- mice as compared with wildtype mice. (FIG. 8D-E) Intravital microscopy was used to determine the number of cells that had emigrated into the cremaster muscle during a 60 minute exposure to MIP2 (2.5 μM) (d) in TLR2-/- mice in the presence or absence of FSL1-Lin2 (200 ng/mL) or (FIG. 8E) in wild-type mice in the presence or absence of FSL1-Lnn2 (200 ng/mL).

(FIG. 9A) Luminescent E. coli were grown in culture in the presence of increasing amounts of GML and monitored for any differences in growth kinetics as a result of the presence of GML. (FIG. 9B) Wild-type or TLR2-/- bone marrow derived macrophages were incubated for 60 min with either FITC-FSL1 (green) or FITC-GML (green) and fixed and stained for the golgi marker Giantin (red).

(FIG. 10A) Wild-type mice were evaluated using intravital microscopy for the number of neutrophils emigrated into the cremaster tissue following superfusion of MIP2 (2.5 μM), MIP2 (2.5 μM)+Rosiglitazone (5 μM), or Rosiglitazone alone (5 μM). (FIG. 10B) Wild-type and TLR2-/- bone-marrow derived macrophages were treated as indicated and evaluated for the production of the cytokine TNFα in response to LPS (100 ng/mL), in the presence or absence of the PPARγ agonist Rosiglitazone (10 μM) and/or the PPARγ inhibitor GW9662 (10 μM). (FIG. 10C) MPO-/- mice evaluated using intravital microscopy for the number of neutrophils emigrated into the cremaster tissue following intrascrotal injections of 150 μl saline containing GML (37.5 ng/g), TNFα (20 ng/g), or TNFα+GML. (FIG. 10D) Male mice were treated with an intrascrotal injection of TNFα (20 ng/g) in the presence or absence of GML (37.5 ng/g) for 4.5 hr or the cremaster was exteriorized and treated with MIP2 (5 μM) in the presence or absence of GML (5 μg/mL) for 60 min. The cremasters were then excised and fixed and stained with hematoxylin and eosin and differential cell counts were determined (FIGS. 10E-F) Percentages of neutrophils (GFP$^{hi}$ cells) were determined by flow cytometry from whole blood and isolated lymph nodes from LysM-eGFP mice following systemic administration of 300 μl saline alone or saline containing, Pam3CSK4 (100 μg) or GML (200 μg) for 16 hr, or a local administration of 150 μl of saline alone or saline containing Pam3CSK4 (10 ng/g) or GML (37.5 ng/g) for 4.5 hr.

FIG. 11. TLR2 lipopeptide ligands.

FIG. 17. Polymorphic neutrophil counts in liver tissue from murine study shown in FIG. 12. Representative spanning disc intravital microscopy images of the liver of an S. aureus-treated mice demonstrating an abundance of intravascular neutrophils (violet; Ly6G$^+$ cells). The images collected from 3 mice per each group were quantitatively analysed to obtain neutrophil counts in the liver. Data are presented as mean±SEM.

FIG. 18. Neutrophil extraceullular traps: neutrophil elastase and histone staining in liver tissue from murine study shown in FIG. 12. Intravascular NETs are released in liver sinusoids during S. aureus infection. Spanning disc intravital microscopy revealed the presence of intravascular NETs consisting of histones (H2Ax, red), and granule proteins (neutrophil elastase, blue). Quantitative analysis of NETs within the livers of mice that were treated with GML or saline is presented on the graphs. Data are presented as mean±SEM.

FIG. 19. Summary of effects of GML on *S. aureus* systemic infection (FIG. 13-18).

FIG. 20. Sterile tissue injury. Change in neutrophil (light dots) recruitment to injured liver (dead cells are propidium iodide positive—diffuse grey areas in center) between control (CTRL; top) and GML (middle), quantified at bottom.

DESCRIPTION OF ILLUSTRATIVE EMBODIMENTS

Figure 7:
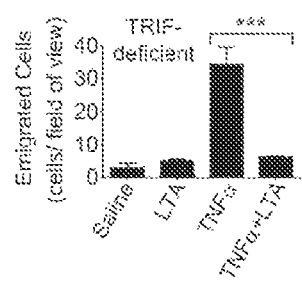
FIG. 7. Inhibitory effect of the LTA preparations is still evident in TRIF-deficient mice. TRIF-deficient mice were given an intrascrotal injection of 150 μl saline containing LTA (5 ng/g), TNFα (20 ng/g), or both together and evaluated after 4.5 hrs for the number of emigrated cells in the cremaster tissue using intravital microscopy.

The inventors have demonstrated that, although TLR receptors and their ligands have been consistently characterized as activators of the immune response, the TLR2 ligand lipotechoic acid (LTA), as well as specific modified TLR2 lipopeptide ligands, can actively inhibit the neutrophil recruitment induced in vivo in response to a wide variety of pro-inflammatory stimuli. In addition, they were able to identify the intracellular signaling mechanism underlying this inhibitory phenomenon, which relies on a previously unrecognized collaboration between TLR2 and the anti-inflammatory, nuclear hormone receptor, Peroxisome Proliferator-Activated Receptor γ, PPARγ (Straus and glass, 2007). These, and other aspects of the invention, are set out in detail below.

I. Toll-Like Receptors

The innate immune system (macrophages, neutrophils, natural killer cells and the alternative complement pathway) is an early and rapid response system to microbial infection. The actions against the invading pathogens are either direct (e.g., phagocytosis and killing) or indirect through the release of cytokines or other stimulatory molecules, which trigger the adaptive immune system by activating B cells and T cells.

Janeway (1992) and Poltorak et al. (1998) proposed that the innate immune system identifies infectious agents by means of conserved structural features through pattern recognition receptors (PRRs). Microbial agents that trigger the immune response are termed pathogen-associated molecular patterns (PAMPs). The discovery of the Toll-like receptors (TLRs) provided the PRRs that detect these PAMPs.

TLRs are critical pattern recognition molecules that signal the presence of a microbial pathogen (Means et al., 2000; Casadevall et al., 1999). These receptors are capable of recognizing highly conserved microbial constituents, and in so doing, they play a major role in host-pathogen interaction. Humans have one of the most active host immune responses to microbial antigens, but this heightened sensitivity makes humans more susceptible to bacterial toxins like lipopolysaccharide (LPS), more so than most any other mammalian species (Heumann et al., 1998).

Toll was originally described in *Drosophila* as a type I transmembrane receptor that controls dorsal-ventral polarity during embryogenesis (Stein et al. 1991). The 18Wheeler (18W) protein is a homolog of *Drosophila* Toll. Toll and 18W share the greatest similarity to each other, as well as to the cytoplasmic tail of the mammalian IL-1R1. The extracellular regions of Toll and 18W contain multiple leucine-rich repeats and carboxyl-terminal cysteine-rich domains (Eldon et al., 1994).

The TLRs of different species are very different: mouse TLR4 and human TLR4 are only 53% identical. Genetic studies of leucine-rich repeat structures among different individuals also revealed that polymorphisms are responsible for a different reaction on microbial challenge. The intracellular part contains a cytoplasmic domain of approximately 200 amino acids that is evolutionarily conserved. This highly conserved region is known as the TIR domain (O'Neill, 2000).

The mammalian homologs of *Drosophila* Toll are known as TLRs. To date, ten human TLRs have been described (Medzhitov et al., 1997; Chaudhary et al., 1998; Takeuchi et al., 1999; Du et al., 2000). TLR1-TLR6 have been characterized by their distinctive expression patterns with mRNA detection assays. TLR1 is expressed ubiquitously and at rather high levels. TLR2 have been known to be expressed in peripheral blood mononuclear cells, as well as in lymphoid tissue (Yang et al., 1999). TLR3 is expressed in lung, muscle, heart, brain and intestinal cells, with alternative splicing reported in pancreas and placenta. Among peripheral blood cells, TLR3 is selectively expressed in specific subsets of dendritic cells (Kadowaki et al., 2001). TLR4 was known to be expressed by monocytes/macrophages, dendritic cells, lymphocytes, the spleen and the heart. TLR5 mRNA is found in peripheral blood monocytes, leukocytes, the ovary and the prostate. TLR6 expression is found in the spleen, the thymus, the ovary and the lung (Takeuchi et al., 1999). TLR mRNA is also expressed in various epithelial cells (Cario et al., 2000), suggesting a role in monitoring for invading microbes.

A. Functional Roles

TLR2. TLR2 is one of the most extensively studied members of mammalian homologs to *Drosophila* Toll. TLR2 requires the adapter protein MyD88 for signaling, and immunoprecipitation studies showed direct interaction of MyD88 and IRAK (Medzhitov et al., 1998). MyD88 was originally isolated and characterized as a myeloid differentiation primary response gene. MyD88 itself consists of a carboxyl-terminal TIR domain. IRAK has been shown both to interact with both MyD88 and TRAF6 (Chaudhary et al., 1998).

TLR2 forms heterodimeric structures with other TLR members such as TLR1 and TLR6. A recent report demonstrated that the p85 regulatory subunit of phosphatidylinositol-3'-kinase can directly associate with the intracellular domain of TLR2 (Arbibe et al., 2000), and the Rho-type GTPase Rac1 also appears to be associated with TLR2-mediated signaling. This alternative pathway activates a number of phosphorylated lipids, resulting in the generation of the intracellular protein kinase Akt. This pathway directly activates NF-κB, independent of the phosphorylation and degradation of I-κB (Arbibe et al., 2000).

B. Ligands

TLR2 has been recognized as a signal transducer for numerous bacterial products. Previously reported TLR2 ligands include lipoteichoic acid, synthetic lipopeptides (Pam$_3$CSK$_4$, MALP-2) and the yeast-derived Zymosan. Table 1, below, provides an extensive list of TLR 2 ligands.

TABLE 1

TLR Ligands

| Receptor (human/mouse) | Microbial Structure | Microorganism | Cellular distribution |
|---|---|---|---|
| (h/m) TLR1/2 | Triacylated lipopeptides | Bacteria (Zahringer et al., 2008) | Cell Surface |
|  | B subunit of type IIb enterotoxin | Escherichia coli (Liang et al., 2008) |  |
|  | Di-acylated lipopeptides | Bacteria (Zahringer et al., 2008) |  |
| (h/m) TLR2/6 | Lipoteichoic Acid Di-acylated lipopeptides | Gram-positive bacteria (Zahringer et al., 2008) Mycoplasma (Zahringer et al., 2008) | Cell Surface |
| (h/m) TLR2 | Lipoproteins Lipoarabinomannan Porins Hepatitis C core and NS3 proteins EBV-encoded dUTPase GPI anchors Phospholipomannan Zymosan Histoplasma capsulatum Yps3p Apolipoprotein CIII gp96 (HSP) Hyaluronan ECM Biglycan | Various Microbes (Buwitt-Beckmann et al., 2006; Kurokawa et al., 2009; Asai et al., 2007; Pecora et al., 2006) Mycobacteria (Means et al., 1999) N. meningitides (Burke et a., 2007; Massari et al., 2006; Chang et al., 2007) Virus (Chang et al., 2007) Virus (Ariza et al., 2009) Protozoa (Debierre-Grockiego et al., 2007; Krishnegowda et al., 2005) Candida (Li et al., 2009) Fungi (Sato et al., 2003; Underhill, 2003) Fungi (Aravalli et al., 2008) Host (Kawakami et al., 2008) Host (Huang et al., 2009) Host (Termeer et al., 2002; Jiang et al., 2005) Host (Schaefer et al., 2005) | Cell Surface |

II. Inflammatory Disease States

In accordance with the present invention, the modified TLR2 ligands disclosed herein will be useful for treating a variety of inflammatory disease states. Exemplary disease states are described below.

A. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis. Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:

heart rate>90 beats per minute
body temperature<36 (96.8° F.) or >38° C. (100.4° F.)
hyperventilation (high respiratory rate)>20 breaths per minute or, on blood gas, a $P_aCO_2$ less than 32 mm Hg
white blood cell count<4000 cells/mm$^3$ or >12000 cells/mm$^3$ (<4×10$^9$ or >12×10$^9$ cells/L), or greater than 10% band forms (immature white blood cells).

Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

B. MRSA

*Staphylococcus aureus* is a major human pathogen, causing a wide variety of illnesses ranging from mild skin and soft tissue infections and food poisoning to life-threatening illnesses such as deep post-surgical infections, septicaemia, endocarditis, necrotizing pneumonia, and toxic shock syndrome. These organisms have a remarkable ability to accumulate additional antibiotic resistance determinants, resulting in the formation of multiply-drug-resistant strains. Methicillin, being the first semi-synthetic penicillin to be developed, was introduced in 1959 to overcome the problem of penicillin-resistant *S. aureus* due to β-lactamase (penicillinase) production (Livermore, 2000). However, methicillin-resistant *S. aureus* (MRSA) strains were identified soon after the introduction of methicillin (Barber, 1961; Jevons, 1961). MRSA have acquired and integrated into their genome a 21- to 67-kb mobile genetic element, termed the *Staphylococcus* cassette chromosome mec (SCCmec) that harbors the methicillin resistance (mecA) gene and other antibiotic resistance determinants (Ito et al., 2001; Ito et al., 2004; Ma et al., 2002). The mecA gene encodes an altered additional low affinity penicillin-binding protein (PBP2a) that confers broad resistance to all penicillin-related compounds including cephalosporins and carbapenems that are currently some of the most potent broad-spectrum drugs available (Hackbarth & Chambers, 1989). Since their first identification, strains of MRSA have spread and become established as major nosocomial (hospital-acquired (HA)-MRSA) pathogens worldwide (Ayliffe, 1997; Crossley et al., 1979; Panlilio et al., 1992; Voss et al., 1994). Recently, these organisms have evolved and emerged as a major cause of community-acquired infections (CA-MRSA) in healthy individuals lacking traditional risk factors for infection, and are causing community-outbreaks, which pose a significant threat to public health (Begier et al., 2004; Beilman et al., 2005; Conly et al., 2005; Gilbert et al., 2006; Gilbert et al., 2005; Harbarth et al., 2005; Holmes et al., 2005; Issartel et al., 2005; Ma et al., 2005; Mulvey et al., 2005; Robert et al., 2005; Said-Salim et al., 2005; Vandenesch et al., 2003; Vourli et al., 2005; Wannet et al., 2005; Wannet et al., 2004; Witte et al., 2005; Wylie & Nowicki, 2005).

The incidence of MRSA infection has greatly increased over the past decade due to the spread of community-associated MRSA. The two predominant strains of CA-MRSA circulating in North America belong to pulsed-field gel types USA300 and USA400 strains according to the CDC classification. The USA300 and USA400 stains have been associated with serious infections including soft tissue abscesses, cellulitis, necrotizing fasciitis, severe multifocal osteomyelitis, bacteremia with Waterhouse-Frederickson syndrome, septic shock and necrotizing pneumonia (Beilman et al., 2005; CDC, 2003; Conly et al., 2005; Francis et al., 2005; Kazakova et al., 2005). Of greater concern is the high transmissibility of USA300 and the link between both USA300 and USA400 and disease outbreaks worldwide (Kazakova et al., 2005; Pan et al., 2003; Tenover et al., 2006). Another alarming observation is that community-associated MRSA strains, in particular USA300, are being reported as causing hospital acquired MRSA infections as well (Bratu et al., 2005; Chalumeau et al., 2005; Linde et al., 2005; Naas et al., 2005).

The USA400 strain is represented by strain MW2, isolated in 1998 in North Dakota from a pediatric patient with fatal septicaemia (1999). The MW2 genome has been fully sequenced and shown to contain 4 genomic islands (vSa3, vSa4, vSaα and vSaβ) 2 prophages (φSa2mw and φSa3mw) and an SCCmec element (IVa), all of which contribute to its virulence (Baba et al., 2002). MW2 is a hypervirulent strain carrying a large number of toxin genes, including new allelic forms of enterotoxins L (sel2) and C (sec4) on vSa3, 11 putative exotoxins (set16-26) on vSaα, lukD and lukE leukotoxins on vSaβ, enterotoxin A (sea), Q (seq) and 2 new allelic forms of enterotoxin G (seg2) and K (sek2) on prophage φSa3mw (Baba et al., 2002). Prophage φSa2mw harbours the lukS-PV and the lukF-PV genes, encoding the PVL components (Baba et al., 2002). Also found in the MW2 genome, but not associated with genomic islands or prophages, are the genes encoding γ-hemolysin (hlg) and enterotoxin H (seh) (Baba et al., 2002).

The USA300 strain, represented by strain FPR3757, was isolated in 2000 from an inmate in a California prison (2001). It has been sequenced and similar to USA400, found to contain multiple genetic elements which contribute to virulence, including an SCCmec element (IVa), 2 prophages (φSa2usa and φSa3usa), 3 pathogenicity islands (SaPI5, vSaα and vSaβ) and the Arginine Catabolic Mobile Element (ACME) (Diep et al., 2006). In contrast to the USA400 genome, which bears a large number of toxin genes, the genome of USA300 carries a smaller number of toxin genes, including enterotoxins K and Q on SaPI5 and set30-39 on vSaα. Prophage φSa2usa is very similar in structure to φSa2mw and, likewise, carries the PVL genes, lukS-PV and lukF-PV. Unique to the USA300 genome is the presence of a 30.9 kb ACME complex. The ACME complex is integrated into the chromosome at the same attachment site as SCCmec and contains an arc gene cluster, encoding an arginine deiminase pathway, as well as a putative oligopeptide permease operon, Opp (Diep et al., 2006). In addition to USA300 strain, the ACME complex has been found in *Staphylococcus capitis* and *Staphylococcus epidermidis*, but due to its high frequency of occurrence in *S. epidermidis* it is believed to have transferred to USA300 from this species (Diep et al., 2006).

The USA300 and USA400 strains belong to multi-locus sequence typing (MLST) type 8 (ST8) and ST1, respectively and both carry Panton-Valentine leukocidin (PVL) genes and SCCmec type IVa. To date, there is no rapid way to identify and characterize CA-MRSA, but rather numerous time and labor intensive molecular characterization tests. An accurate and rapid PCR based assay, able to distinguish USA300 and USA400 isolates from other MRSA, would facilitate in the identification of outbreaks, treatment of patients and aid in the implementation of control measures designed to limit the spread of these serious pathogens.

C. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

D. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

E. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation (≥2 weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

F. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

G. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels.

Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:

higher fibrinogen and PAI-1 blood concentrations
hlevated homocysteine, or even upper half of normal
elevated blood levels of asymmetric dimethylarginine
high inflammation as measured by C-reactive protein
levated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

H. Autoimmune/Inflammatory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

The term "inflammatory bowel disease" or "IBD," as used herein, describes a broad class of diseases characterized by inflammation of at least part of the gastrointestinal tract. IBD symptoms may include inflammation of the intestine and resulting in abdominal cramping and persistent diarrhea. Inflammatory bowel diseases include ulcerative colitis (UC), Crohn's disease (CD), indeterminate colitis, chronic colitis, discontinuous or patchy disease, ileal inflammation, extra-colonic inflammation, granulomatous inflammation in response to ruptured crypts, aphthous ulcers, transmural inflammation, microscopic colitis, diverticulitis and diversion colitis.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

Crohn's disease is characterized by intestinal inflammation and the development of intestinal stenosis and fistulas; neuropathy often accompanies these symptoms. One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Soderholm et al., 1999; Hollander et al., 1986; Hollander, 1992). Another hypothesis is that persistent intestinal infection by pathogens such as *Mycobacterium paratuberculosis*, *Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce (Sartor, 1997). The presence of IgA and IgG anti-*Sacccharomyces cerevisiae* antibodies (ASCA) in the serum was found to be highly diagnostic of pediatric Crohn's disease (Ruemmele et al., 1998; Hoffenberg et al., 1999).

I. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

J. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

III. Methods of Treatment

The modified TLR2 ligands of the present invention are generally useful as anti-inflammatories. They can be administered to mammalian subjects (e.g., human patients) who exhibit symptoms of inflammatory disease such as those discussed above. The compounds can also be administered to subjects that are genetically and/or due to, for example, physiological and/or environmental factors, susceptible to inflammation, e.g., subjects with a family history of inflammatory disease, or subjects with chronic inflammation or subject to chronic stress.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the ligand in a suitable delivery vehicle (e.g., polymeric microparticles or implantable devices) may increase the efficiency of delivery, particularly for oral delivery.

It is common in many fields of medicine to treat a disease with multiple therapeutic modalities, often called "combination therapies." Inflammatory diseases are no exception. To treat inflammatory disorders using the methods and compositions of the present invention, one would generally contact a target cell, site or subject with a modified ligand according to the present invention and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the modified ligand and the other includes the other agent.

Alternatively, the modified ligand may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment signifi-cantly; however, where several days (2, 3, 4, 5, 6 or 7) to several weeks (1, 2, 3, 4, 5, 6, 7 or 8) lapse between the respective administrations.

It also is conceivable that more than one administration of either the modified TLR2 ligand or the other therapy will be desired. Various combinations may be employed, where the modified TLR2 ligand is "A," and the other therapy is "B," as exemplified below:

| |
|---|
| A/B/A B/A/B B/B/A A/A/B B/A/A A/B/B B/B/B/A B/B/A/B |
| A/A/B/B A/B/A/B A/B/B/A B/B/A/A B/A/B/A B/A/A/B B/B/B/A |
| A/A/A/B B/A/A/A A/B/A/A A/A/B/A A/B/B/B B/A/B/B B/B/A/B |

Other combinations are contemplated.

Agents or factors suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

IV. Pharmaceutical Compositions

It is envisioned that, for administration to a host, TLR2 ligands will be suspended in a formulation suitable for administration to a host. Aqueous compositions of the present invention comprise an effective amount of ligand, factor or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Compositions will generally be formulated for parenteral administration, e.g., formulated for injection via the intravenous, intramuscular, sub-cutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Generally, dispersions are prepared by incorporating the various modified TLR ligands into a sterile vehicle which contains the basic dispersion medium and the required other ingredients for maintaining cell viability as well as potentially additional components to effect proliferation or differentiation in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Mice/Reagents.

C57BL/6 wt, TRIF-deficient and MPO−/−, The Jackson Laboratory, (Bar Harbor, Me.), MyD88−/− and TLR2−/−, kindly provided by Dr. Shizuo Akira, (Osaka University, Japan), and LysMeGFP, by Dr. Thomas Graf, (Albert Einstein College of Medicine, Bronx, N.Y., USA). Chimeric mice were made using bone marrow isolated from donor mice and recipient mice were irradiated with two doses of 5 Gy at an interval of three hours. $8 \times 10^6$ donor bone marrow cells were injected into the tail vein of the recipient irradiated mice. The mice were housed in micro-isolator cages for eight weeks to allow for full humoral reconstitution. This protocol was previously confirmed to show that 99% of leukocytes from Thy1.1 into Thy1.2 congenic recipient mice were donor derived (Carvalho-Tavares et al., 2000). Mice were maintained the pathogen-free facility at the University of Calgary's Animal Resource Center and animal protocols were approved by the University of Calgary Animal Care Committee and met the guidelines of the Canadian Council for Animal Care. Ultra-pure LTA (InvivoGen), and was kindly provided by Dr. Sonja Von Aulock (Konstanz, Germany). All modified ligands as well as R-FSL1 and S-FSL1 (EMC Microcollections GmbH). Pam2CSK4 and Pam3CSK4 (Invivogen), TNFα and MIP2 (R&D Systems), Rosiglitazone (Cayman Chemical), and T0070907 (Tocris).

Intravital Microscopy.

Intravital microscopy was performed on male mice, anaesthetized with an intraperitoneal injection of a 10 mg/kg xylazine (Bayer) and 200 mg/kg ketamine hydrochloride (Rogar/STB). The left jugular vein was cannulated to administer additional anaesthetic when necessary. An incision in the scrotal skin exposed the left cremaster muscle, which was then carefully dissected free of the associated fascia. The cremaster muscle was cut longitudinally with a cautery pen. The testicle and the epididymis were then separated from the underlying muscle and were moved into the abdominal cavity. The muscle was held flat on an optically clear viewing pedestal and was secured along the edges with 4-0 suture. The exposed tissue was superfused with 37° C.-warmed bicarbonate-buffered saline (pH 7.4). An upright microscope (Mikron; Carl Zeiss) was used to examine the cremasteric microcirculation and a video camera (XR/MEGA10-AM or XR/MEGA10 Panasonic) and DVD recorder were used to capture images. Three to five cremasteric venules (25 to 40 μm in diameter) were analysed during playback analysis. A leukocyte was considered to be adherent if it remained stationary for at least 30 seconds, and total leukocyte adhesion was quantified as the number of adherent cells within a 100-μm length of venule. Leukocyte emigration was defined as the number of cells in the extravascular space within the field of view adjacent to the observed venule.

Monitoring *E. coli* Growth.

*E. coli* cultures (derived from the WS2572 clinical isolate from the Weihenstephan Culture Collection) were grown in Luria Broth containing 30 μg/mL kanamycin to an $OD_{600}$ of 0.5, which was taken to be equivalent to $1.1 \times 10^9$ CFU/mL (Georgel et al., 2005). Cultures resuspended in sterile saline at a concentration of $4.0 \times 10^7$ CFU/mL. The cultures were diluted 1:1 with either saline or saline containing the appropriate concentration of LTA or GML, and further diluted 1:1 with sterile Cytodex beads (Sigma) and stored on ice until the time of inoculation. The mice were injected subcutaneously with 50 μl or $5 \times 10^5$ CFU of this bacterial/bead/(+/− LTA or GML) mixture between the scapula, centered on the spine. The mice were housed with food and water ad libitum and treated with analgesic for the entire experimental period. Bacterial growth monitoring required anaesthetising the mice with isoflurane and imaging using the Xenogen IVIS-200 imaging system (Xenogen Imaging Technologies). In vitro, Xen 14 (Caliper Life Sciences) *E. coli* overnight cultures of Luria Broth containing 30 μg/mL kanamycin were diluted 1 in 20 in Luria Broth, containing 30 μg/mL kanamycin, and distributed in 100 μl aliquots in a 96 well fluorescent plate, along with increasing amounts of LTA or GML in 5 μl of saline to different wells in triplicate. These cultures were overlaid with 50 μl of mineral oil and grown overnight at 37° C. The $OD_{600}$ and the luminescence of each well was monitored every 20 min using a Wallac Victor$^2$ 1420, Multilabel Counter (Perkin Elmer).

Cell Culture/Isolation.

Bone marrow derived macrophages were differentiated using bone marrow from 7-10 week-old mice plated in 6-well plates, (Nunc), at a density of $1.5 \times 10^6$ cells/well in 2 mL of bone marrow medium (DMEM media (GIBCO) supplemented with glutamine (200 μM), 100 U/mL penicillin, 100 μg/mL streptomycin (GIBCO), 10% fetal bovine serum (GIBCO), and 10% L929 cell-conditioned media), maintained in a humidified incubator at 37° C. with 10% $CO_2$. On the fifth day of culture 1 mL of bone marrow medium was added to each well. Cells were fully differentiated and used for experiments on the seventh day of culture. Raw264.7 cells grown in RPMI 1640 media (GIBCO), supplemented with 1 mM sodium pyruvate (GIBCO), 100 U/mL penicillin and 100 μg/mL streptomycin (GIBCO), 50 μM 2-mercaptoethanol (Sigma), and 10% (v/v) fetal bovine serum (GIBCO), in a humidified incubator at 37° C. with 5% $CO_2$.

SDS PAGE/Western Blotting.

Laemmli's buffer lysates were loaded onto 10% polyacrylamide gels for electrophoresis and subsequently transferred to nitrocellulose (Scleicher & Schuell). Nitrocellulose membranes were blocked for one hour in TBS-0.1% Tween containing 5% Fraction V bovine serum albumin (Roche). Membranes were then incubated overnight with primary antibody (Long et al., 2009).

Statistical Analysis.

All results are presented using GraphPad Prism5™ software and are expressed as mean±SEM. A t-test was applied for analysis between two groups, a one-way analysis of variance with Bonferroni multiple comparisons adjustment was applied for multiple comparisons between groups and a two-way analysis of variance with Bonferroni post test was applied for time-course experiments, (*p≤0.05 p≤0.01 *p≤0.001). All results presented n≥3.

RT-PCR.

Cells were treated as described for individual experiments and total RNA was isolated using Trizol™ (Invitrogen) and treated with DNase (Promega) in the presence of 20 units RNase Block (Invitrogen). Following DNase treatment the RNA was phenol:chloroform extracted to remove the DNase. 2 µg of RNA was used to make cDNA using Superscript II (Invitrogen). 1 µl of this cDNA reaction was then used to perform PCR, using Taq polymerase (Invitrogen).

Enzyme-Linked Immunosorbant Assays.

ELISAs were performed as per the manufacturer's instructions; IL6 (BD Biosciences), IL12 (Peprotech Inc.) and TNFα (Peprotech Inc.).

Intravital Measurements.

The average rolling velocity was measured in each vessel by monitoring the average length of time required for twenty randomly selected leukocytes to roll a distance of 100 µm (µm/sec).

Internalization of FITC-FSL1/GML.

Bone marrow-derived macrophages were isolated from wild-type and TLR2−/− mice and cultured on glass coverslips. The cells were incubated on ice for 10 min in the presence of 10 µg/mL FITC-FSL1 or FITC-GML to allow ligands binding and then returned to 37° C. for 60 min. Cells were then fixed for 10 minutes in 4.5% paraformaldehyde and stained for the golgi marker Giantin (1:250, Abcam), and imaged using confocal microscopy.

Neutrophil Whole Blood and Lymph Node Counts.

Male LysM-eGFP mice, which express green fluorescent protein predominantly in neutrophils, were given an intrascrotal injection of 150 µl saline (4.5 hrs) or an intraperitoneal injection of 300 µl saline (16 hr). Whole blood and lymph nodes were isolated from these animals and the percent neutrophils per total cells was evaluated using flow cytometry for GFP$^{hi}$ cells.

Cremaster Histology.

Wild-type male C57/B6 mice were given an intrascrotal injection of saline, (150 µl), or saline containing various pro-inflammatory ligands, or superfused with buffer containing pro-inflammatory ligands, as described in the results. Four hours following ligand administration the cremaster muscle was exteriorized, cut off, and fixed in 10% formalin. The cremaster tissue was embedded in paraffin and 5 µm sections were cut and stained with haematoxylin and eosin. The numbers of lymphocytes, monocytes, and neutrophils in the post capillary venules were counted and differential percentages were scored.

Sterile Inflammation.

Mice were anesthetized with a mixture of ketamine hydrochloride (200 mg/kg, Rogar/SBT) and xylazine hydrochloride (10 mg/kg, MTC Pharmaceuticals). After anesthesia, the right jugular vein was cannulated for administration of additional anesthetic and for injection of additional anaesthesia during experiments.

Mice were prepared for intravitial microscopy of the liver by performing a midline laparotomy followed by removal of the skin and abdominal muscle along the costal margin to the mid-axillary line to expose the liver. Mice were placed in the right lateral position and a single liver lobe was exteriorized on the pedastal of a custom-made Plexiglas microscope stage. All exposed tissues were moistened with saline-soaked gauze to prevent dehydration during imaging. For the duration of all experiments, body temperature was maintained with an infrared heat lamp, and the liver was continuously superfused with physiological saline buffer. Exposed tissues were visualized with an Olympus BX51 upright microscope equipped with a confocal light path (Wave-Fx; Quorum) based on a modified Yokogawa CSU-10 head (Yokogawa Electric Corporation) using a ×4/0.16 UplanSApo objective or ×10/0.30 UplanFL N objective. Neutrophils were visualized by expression of eGFPhi (versus eGFPlow monocytes and macrophages) in LysM-eGFP mice (gift from Dr. T. Graf (Albert Einstein University, NY). Necrotic cells were visualized by superfusion of the liver surface with 2 µM propidium iodide.

For experiments investigating the quantity of adherent neutrophils at sites of focal necrosis, images were acquired four hours after injury using a 4× objective with the injury in the center of the field of view. The total number of adherent neutrophils was then determined per field of view. Neutrophils were considered adherent if they remained stationary for 30 seconds or longer.

After preparation for intravital microscopy and immediately prior to imaging, a single 0.022±0.001 mm$^3$ focal injury was induced on surface of the liver to a depth of ~80 µm using the tip of a heated 30-gauge needle mounted on an electro-cautery device. Necrotic cells were immediately labeled with a single application of 50 µL of 2 µM propidium iodide solution to the surface of the liver. In the presence of GML, the GML was included in the superfusion buffer and superfused at a concentration of 25 mg/mL.

In Vivo Studies—Sepsis Model.

Figure 12:
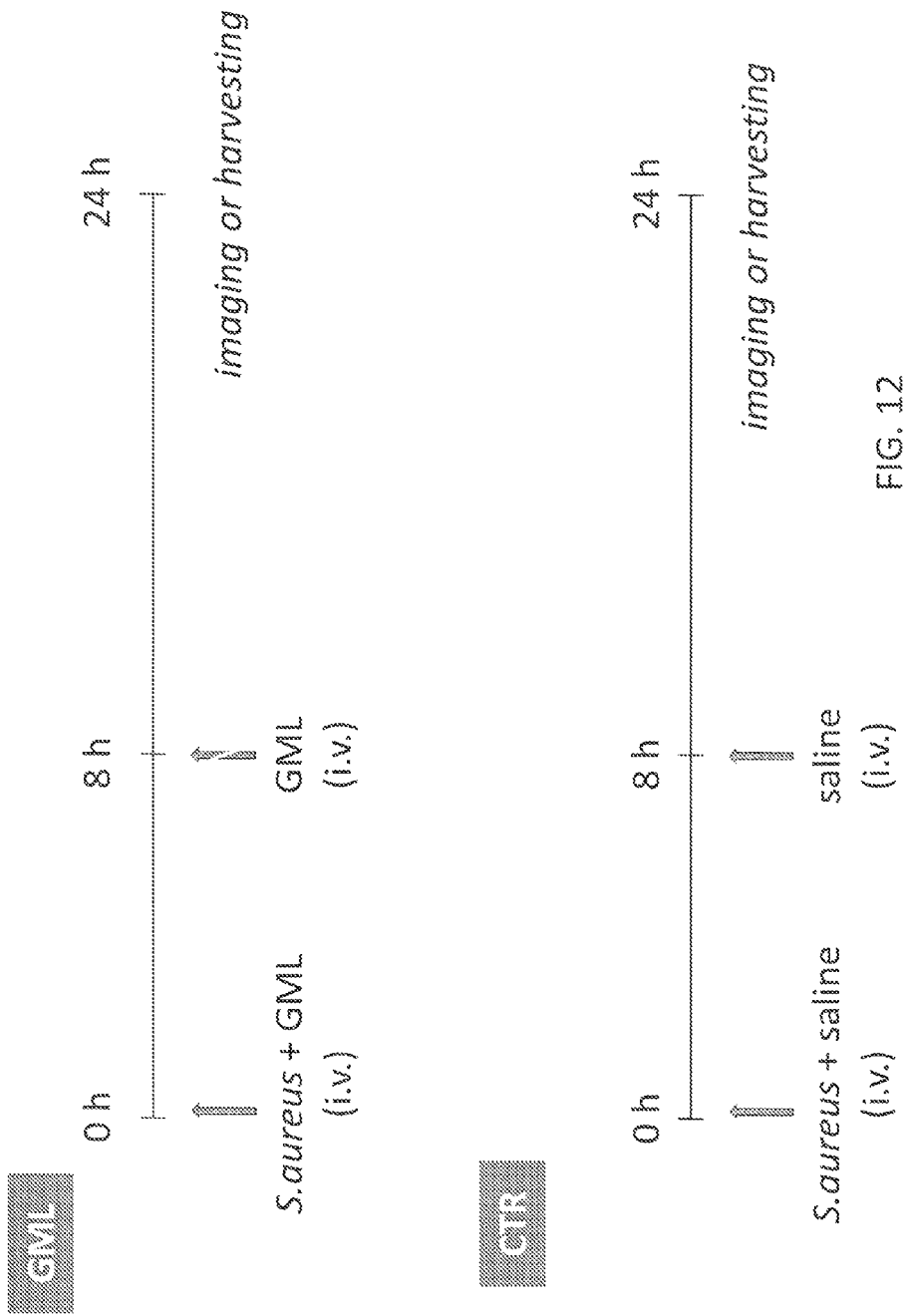
FIG. 12. Experimental design for mouse studies on the Staphylococcus aureus sepsis model. S. aureus (US300 community acquire-MRS) was injected i.v. at time 0 (1-5×10$^7$ CFUs/mouse). In experimental animals the initial S. aureus administration was supplemented with GML and was followed by the second GML treatment at 8 hrs. Control animals received saline instead of GML at the same time points.

The methicyllin-resistant *Staphylococcus aureus* (MRSA) USA300-2406 was isolated from a septic patient at the Foothills Hospital in Calgary. *S. aureus* was grown in brain heart infusion BHI (chloramphenicol 20 µg/ml) at 37° C. overnight. Bacteria were subcultured in fresh BHI and incubated for 2 hrs in a 37° C. shaker to obtain bacteria in mid-log phase growth prior to injection. Mice were treated with an intravenous injection of 1-5×10$^7$ CFUs of *S. aureus* in a volume of 200 microliters of saline. Experimental animals received the *S. aureus* injection supplemented with GML and the GML i.v. shot was repeated 8 hrs later. Control animals received the same treatments with saline (FIG. 12). At 24 hours post-infection, animals were either used for intravital observations of the liver or were euthanized under anesthesia. The lungs and liver were harvested, weighed, placed in 1 mL of sterile PBS, and homogenized with an electric tissue homogenizer.

Lung Injury Assessment—MPO.

The lungs of anaesthetized mice were removed after specified period of reperfusion. For determination of lung myeloperoxidase (MPO) activity (an indicator of inflammation), samples of lungs were removed, weighed, immediately frozen in liquid nitrogen and stored at −80° C. until the MPO activity assay was performed. Myeloperoxidase activity was measured using an assay previously described (Krawisz et al, Gastroenterology. 1984; 87:1344-50) and modified to be used in a 96-well microtitre plate. Values are expressed as units of MPO activity per milligram of lung tissue (U/mg tissue).

Liver Injury Assessment.

ALT Serum levels of alanine aminotransferase (ALT) were detected in blood obtained via cardiac puncture as an indicator of hepatocellular injury. A commercially available diagnostic kit (Biotron Diagnostic) was used to quantify serum levels of ALT. Results are expressed as International Units per liter of serum.

Evaluation of Liver Damage Areas.

The livers of euthanized mice were removed and immediately placed in ice-cold PBS. Images were captured via a digital camera and the areas of liver damage were measured and analysed with ImageJ.

Bacteriological Analysis.

For determination of colony forming units (CFU), 10 μl of tissue homogenate of the liver and the lung was serially diluted, plated onto brain heart infusion (BHI) agar, incubated at 37° C. for 18 h, and bacterial colonies were counted.

Intravital Imaging of NETs the Liver.

Liver imaging.

A midline abdominal incision was made through the skin and linea alba to open the peritoneal cavity. The skin and abdominal wall were removed using electrocautery along the costal margin to the mid-axillary line to expose the liver Animals were placed in the left lateral position on a custom-made plexiglass microscopy stage, allowing the left lobe of the liver to rest on a glass coverslip over the microscope objective. Exposed abdominal contents were covered with saline-soaked gauze for the duration of the experiment. The exposed liver lobe was stabilized with a small piece of tissue paper, and was continuously superfused with warm saline solution. The exposed liver lobe was visualized with an Olympus IX81 inverted microscope equipped with a confocal light path (Wave-Fx; Quorum) based on a modified Yokogawa CSU-10 head (Yokogawa Electric Corporation) using a UPLANSAPO 10×/0.40 or UPLANSAPO 20×/0.70 air objectives. Three laser excitation wavelengths (488-, 561-, and 635-nm; Cobalt) were used in rapid succession and visualized with the appropriate long-pass filters (Semrock). Exposure times for excitation wavelengths were 303 ms (488-nm), 303 ms (561-nm), and 300 ms (635-nm). A back-thinned EMCCD 512×512 pixel camera (C9100-13, Hamamatsu, Bridgewater, N.J.) was used for fluorescence detection. Volocity acquisition software (Improvision) was used to drive the microscope.

NET Staining.

Fluorescence imaging of NETs components was performed using intravital immunofluorescence analysis. Extracellular histone H2Ax was labeled with Alexa-fluor 555-anti-mouse H2Ax antibody (5 μg), and neutrophil elastase (NE) was labeled with Alexa-fluor 647-anti-mouse NE antibody (0.6 μg). Neutrophils were visualized by injection of Alexa-fluor 750-anti-mouse Gr-1 antibody (3 μg). All antibodies and dyes were injected i.v. 15 minutes prior to intravital imaging.

Analysis of Liver Intravital Imaging Videos.

Images from individual color channels (eg. red for histone H2Ax, far red for NE) were exported and analyzed in ImageJ (NIH). To account for differences in background fluorescence between experiments and antibody lots and to eliminate background autofluorescence, contrast was adjusted to eliminate autofluorescent background staining, and a minimum brightness threshold was set to yield only positive staining. The same contrast and threshold values were applied to all images from all treatment groups within the experiment. Thresholded images were converted to binary (black and white), and the area per field of view covered by positive fluorescence staining (black) was calculated using ImageJ software. Data are expressed as the percentage of area in each field of view covered by positive fluorescence staining.

Example 2

Results

The TLR2/6 Ligand, LTA, Inhibits Acute Neutrophil Recruitment In Vivo.

In previous studies, the inventors have reported that the di-acylated TLR2/6 ligand, LTA, does not induce neutrophil recruitment in vivo when evaluated in a murine model of acute inflammation (Yipp et al., 2002; Long et al., 2009). This is in direct contrast to typical TLR2 lipopeptide ligands, which each induce robust neutrophil recruitment in vivo (Long et al., 2009). The inability of LTA to induce neutrophil recruitment was unexpected and was further complicated by the knowledge that many commercial LTA preparations are contaminated with non-TLR2, pro-inflammatory stimuli, including lipopolysaccharide (LPS) (Morath et al., 2002). Despite the presence of these potent pro-inflammatory contaminants, these preparations, as well as ultrapure preparations of LTA, did not induce neutrophil recruitment in vivo (Yipp et al., 2002; Long et al., 2009). Considering these data, the inventors developed the hypothesis that LTA is able to inhibit the in vivo neutrophil recruitment induced by other acute inflammatory stimuli. To test this hypothesis, they used intravital microscopy of the murine cremaster muscle and evaluated the degree of neutrophil recruitment following intrascrotal administration of the TLR4 ligand, LPS, or the cytokine, TNFα, in the presence or absence of ultra-pure preparations of *Staphylococcus aureus* LTA. In the presence of LTA, significantly fewer neutrophils emigrated into the cremaster muscle as compared with LPS or TNFα alone (FIG. 1A). In fact, the number of emigrated cells in the presence of LTA was similar to base-line, non-inflamed conditions (FIG. 1A). This inhibitory response to LTA treatment was not observed in TLR2−/− mice (FIG. 1A) and using bone-marrow chimeric mice, the inventors found that TLR2 expression is required on bone-marrow-derived cells in order to observe the inhibitory response (FIG. 1B). Since systemic inflammatory responses can lead to neutrophil trapping in the liver and lung (Kerfoot and Kubes, 2005), the inventors evaluated circulating leukocyte counts in order to ensure that the reduced emigration observed in wild-type animals was not due to neutrophil trapping in the aforementioned organs and associated neutropenia. In each treatment scenario, the counts were unchanged from the control saline treatment (FIG. 6A). In contrast to the emigration data, the neutrophils were induced to roll slowly along the endothelium in response to LPS and TNFα and this was unaffected by LTA co-treatment, (FIG. 6B), suggesting no untoward toxic effects on the neutrophils.

To further evaluate the inhibitory potential of LTA, a subcutaneous inoculum of a luciferase reporter *E. coli* strain was used as a complex inflammatory ligand source. When LTA was co-administered with this live bacterial inoculum, the host response was delayed, as observed by a prolonged presence of the reporter strain in animals that had received LTA (FIGS. 1C and 1D). This observation was not due to a general ability of LTA preparations to promote the growth of *E. coli*, as the presence of LTA had no effect on bacterial growth in vitro (FIG. 6C). In order to examine the inhibitory capacity of LTA towards direct chemokine stimulation, MIP2 was perfused over the exposed cremaster, in the presence or absence of LTA. In this scenario, neutrophil emigration was also inhibited in the presence of LTA (FIG. 1E). These results encouraged the examination of the potential for LTA preparations to intervene during established acute inflammatory reactions. To test this, mice were given intrascrotal injections containing LPS or TNFα, and 2 hours later the same mice were given intrascrotal injections containing LTA. After another 2.5 hours, the number of emigrated cells was found to be approximately fifty percent reduced in the animals exposed to the LTA preparations (FIG. 1F). Taken together, these data demonstrate that the inhibitory capacity of LTA preparations is not limited to a particular pro-inflammatory stimulus or receptor system, and most importantly, that LTA can interrupt acute inflammatory responses, even after they have been initiated.

Since LTA is routinely used to study TLR2 biology in vitro, the inventors evaluated the inhibitory capacity in murine bone marrow-derived macrophages. They did not see any inhibitory effects and, consistent with the literature (Long et al., 2009), the inventors found LTA to activate inflammatory responses in these cells (FIGS. 6D and 6E). Finally, to determine if this is a general inhibitory property of all TLR2 ligands, or a unique characteristic of LTA preparations, LPS was administered with each of the other TLR2 ligands; R-FSL1, S-FSL1, Pam2CSK4, or Pam3CSK4. These ligands themselves were pro-inflammatory and did not exhibit any inhibitory properties toward neutrophil emigration (FIG. 6F), which is consistent with previous reports (Long et al., 2009).

The Inhibitory Capacity of LTA is MyD88-Independent.

Signaling downstream of TLR2 requires MyD88 (Akira, 2000). The inventors used MyD88−/− mice to evaluate the requirement for TLR2-dependent signaling in the inhibitory response, and found that MyD88 is dispensable for the inhibitory activity of LTA preparations (FIG. 2A). As a control, when conventional signaling pathway activation in bone marrow-derived macrophages was evaluated in vitro in response to LTA, the strict requirement for MyD88 to allow NFκB pathway activation was apparent (FIG. 2B). To eliminate the possibility that the TLR3/TLR4-specific, MyD88-independent pathway is involved, the inventors used TRIF-deficient animals (Yamamoto et al., 2003). LTA inhibited TNFα-induced neutrophil recruitment in these animals to a similar degree as observed in wild-type or MyD88−/− animals (FIG. 7).

Defining the Molecular Characteristics that Render TLR2 Ligands Inhibitory.

LTA is a complex, heterogeneous mixture of up to fifty 1,3-linked polyglycerolphosphate subunits linked to a β-gentiobiose core with a lipid anchor (Morath et al., 2001; Deininger et al., 2007). The inventors chose to focus on the lipid anchor, since specific fatty acids, which can be derived from specific acyl chain modifications, can be modified to yield products with anti-inflammatory properties. In particular, oxidized or nitrated derivatives of linoleic acid and nitrated derivatives of oleic acid, are known PPARγ ligands (Villacorta et al., 2009). Activation of this nuclear hormone receptor has been shown to be anti-inflammatory by limiting neutrophil migration as well as the production of pro-inflammatory mediators by macrophages (Straus and Glass, 2007; Reddy et al., 2008; Jiang et al., 1998). In addition, another fatty acid, linolenic acid, can be metabolized to yield anti-inflammatory mediators of the resolvin and protectin family (Serhan et al., 2008). Unfortunately, the complex structure of LTA does not lend itself easily to chemical synthesis. To overcome this issue and to understand the structure function relationship of TLR2 anti-inflammatory ligands, the inventors took an alternative approach and asked the question: can pro-inflammatory TLR2 ligands be transformed to yield inhibitory ligands through modifications of the acyl chains that incorporate the aforementioned lipids? To address this question, the inventors synthesized modified versions of the pro-inflammatory lipopeptide TLR2 ligand, FSL-1, to contain the lipid modifications of: di-linoleate, di-oleate, or di-linolenate, in lieu of the conventional di-palmitate (FIG. 11). These modified ligands were then used to determine if any of these modifications could transform the pro-inflammatory lipopeptide TLR2 ligand, FSL1, into an anti-inflammatory TLR2 ligand.

Figure 8:
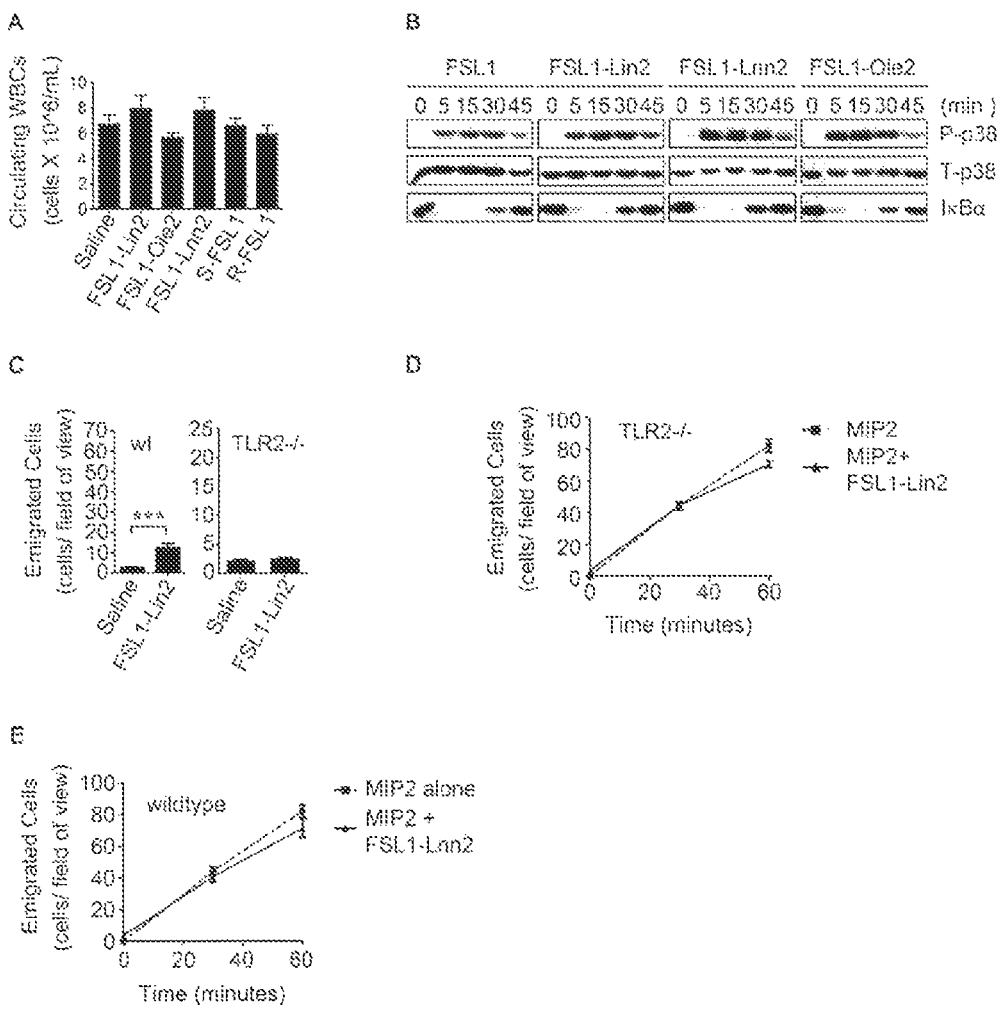
FIGS. 8A-E. Evaluating the in vitro and in vivo responses to the modified FSL1 ligands.

Following intrascrotal administration of the ligand containing di-linoleate, (FSL1-Lin2), neutrophil recruitment was severely compromised when compared with the parent FSL-1 ligand (FIG. 3A). Once again this was not due to an effect on circulating leukocyte counts (FIG. 8A). By comparison, the other engineered ligands, (FSL1-Lnn2 and FSL1-Ole2), each induced emigration to comparable levels as the parent FSL-1 ligand (FIG. 3A). When these ligands were used to stimulate murine macrophages, each ligand similarly activated NFκB and MAP Kinase signaling, indicating competence in stimulating TLR2 (FIG. 8B). The small residual capacity of FSL1-Lin2 to initiate neutrophil recruitment remained dependent upon TLR2 (FIG. 8C). In order to establish whether FSL1-Lin2 is able to inhibit neutrophil recruitment in vivo, the exposed cremaster muscle was superfused with MIP2 in the presence or absence of FSL1-Lin2 for one hour. In a manner that mimicked the inhibitory capacity of LTA preparations, the presence of FSL1-Lin2 inhibited the emigration of cells into the tissue (FIG. 3B) in a TLR2-dependent manner (FIG. 8D), which was not observed using the pro-inflammatory FSL1-Lnn2 ligand (FIG. 8E). These data indicate that imbedding linoleate within the FSL1-Lin2 ligand imparted anti-inflammatory characteristics onto this TLR2 ligand. However, FSL1-Lin2 retained a small capacity to activate inflammatory responses and recruit neutrophils, and thus this ligand did not fully mimic the anti-inflammatory capacity of LTA.

Unlike LTA, FSL1-Lin2 retains a low-level neutrophil recruiting potential when evaluated 4.5 hours following intrascrotal injection (FIG. 3A). The one hour incubation period described above for the inhibition of MIP2-induced neutrophil recruitment, is not enough time for the residual pro-inflammatory capacity of FSL-Lin2 to be a complicating factor. However, in order to evaluate the inhibitory effect towards TNFα-induced neutrophil recruitment, this requires a longer incubation period. In this case, consistent with its residual pro-inflammatory capacity, FSL1-Lin2 does not exhibit any inhibitory potential towards TNFα-induced neutrophil recruitment in wild-type animals, as evaluated 4.5 hours following intrascrotal administration of these stimuli (FIG. 3C). Therefore, the inventors wondered whether removing the residual pro-inflammatory capacity of this ligand would yield a ligand with purely anti-inflammatory properties. To address this question, MyD88−/− mice were used to negate the influence of the pro-inflammatory signaling capacity of FSL1-Lin2 within the 4.5 hour treatment time. In this scenario, FSL1-Lin2 was found to inhibit TNFα-induced neutrophil emigration (FIG. 3C). Therefore, in the absence of the residual pro-inflammatory responses induced by this engineered ligand, its inhibitory capacity is absolute. Taken together these data suggest that, in addition to the acyl chain modifications that yield an inhibitory TLR2 ligand, another aspect of the structure of LTA must impart additional inhibitory potential. In other words, the structure of a TLR2 ligand must completely impede its pro-inflammatory capacity in order to reveal a purely anti-inflammatory TLR2 ligand.

Designing a Synthetic TLR2 Ligand with Purely Anti-Inflammatory Properties: GM1-Targeted, Linoleate-Containing TLR2 Ligand (GML).

Figure 9:
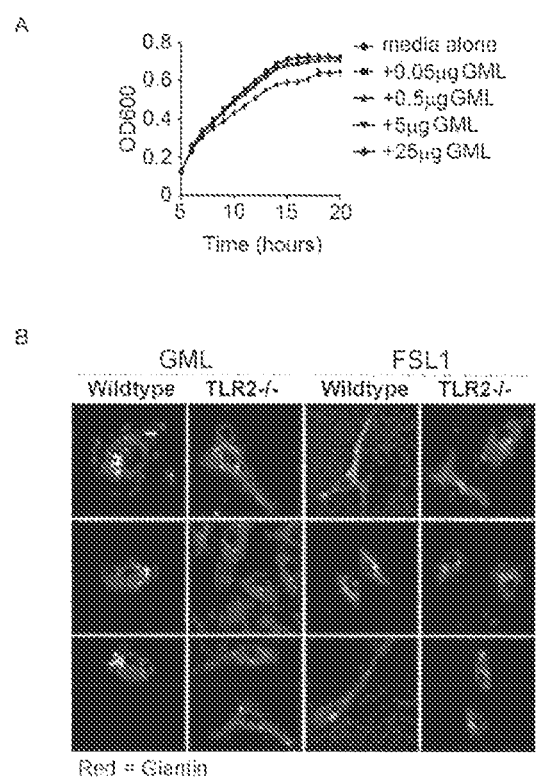
FIGS. 9A-B. Inhibitory characteristics of GML.

The inventors next sought to abrogate the pro-inflammatory capacity of the proof-of-principle TLR2 anti-inflammatory ligand, FSL1-Lin2. The inventors previously published that LTA is not as potently pro-inflammatory as other TLR2 ligands and this may be due to differential cellular internalization mechanisms between LTA and the other TLR2 ligands (Long et al., 2009). Internalized LTA is targeted to the ER, golgi, and endosomal compartments (Nilsen et al., 2008). Artificially retaining LTA on the cell surface and thereby abrogating this internalization allows LTA to activate inflammatory responses much more potently in vitro (Nilsen et al., 2008). Therefore, the inventors sought to further refine FSL1-Lin2, to mimic the internalization program of LTA in an attempt to hamper its pro-inflammatory capacity. To accomplish this, the inventors altered the peptide sequence of the lipopeptide, to a sequence that has been shown to bind the plasma membrane ganglioside, GM1 (Matsubara et al., 1999). This strategy would allow the TLR2 ligand to also bind GM1 in addition to TLR2 and to mimic the internalization mechanisms of the GM1 ligand, cholera toxin, which is also known to accumulate in the golgi (Tarrago-Trani and Storrie, 2007). This so-named, GM1-targeted, linoleate-containing TLR2 ligand (GML), shown in FIG. 4A, was tested for the ability to inhibit neutrophil recruitment. The inventors found that GML mimics the TLR2-dependent, MyD88-independent inhibitory capacity of the LTA preparations (FIG. 4B). Additionally, GML was found to inhibit the clearance of a subcutaneous inoculum of live *E. coli* (FIGS. 4C and 4D), while having no beneficial effect on bacterial growth in vitro (FIG. 9A). GML was also found to inhibit the neutrophil recruitment induced by MIP2 (FIG. 5D). When the internalization of FITC-labelled FSL1 and GML ligands was evaluated in bone-marrow derived macrophages, distinct localization patterns were observed. GML accumulated in larger vesicles than the pro-inflammatory TLR2 ligand, FSL1, and GML partially co-localized with the golgi marker, Giantin (FIG. 9B). FSL1 was found in much smaller vesicles, which did not co-localize with Giantin. TLR2 is involved in the internalization of both ligands, as FSL1 was substantially inhibited with regard to internalization in the absence of TLR2, and GML was no longer associated with the golgi in the absence of TLR2 (FIG. 9B). The residual internalization of GML in the absence of TLR2 may relate to its capacity to bind GM1. In sum, the inventors have been able to define the molecular requirements for a TLR2 ligand to be transformed into an inhibitor of neutrophil recruitment, and in the process, they have designed a synthetic anti-inflammatory TLR2 ligand: GML.

The Inhibitory Activity of LTA and GML Requires Functional PPARγ Signalling.

Figure 10:
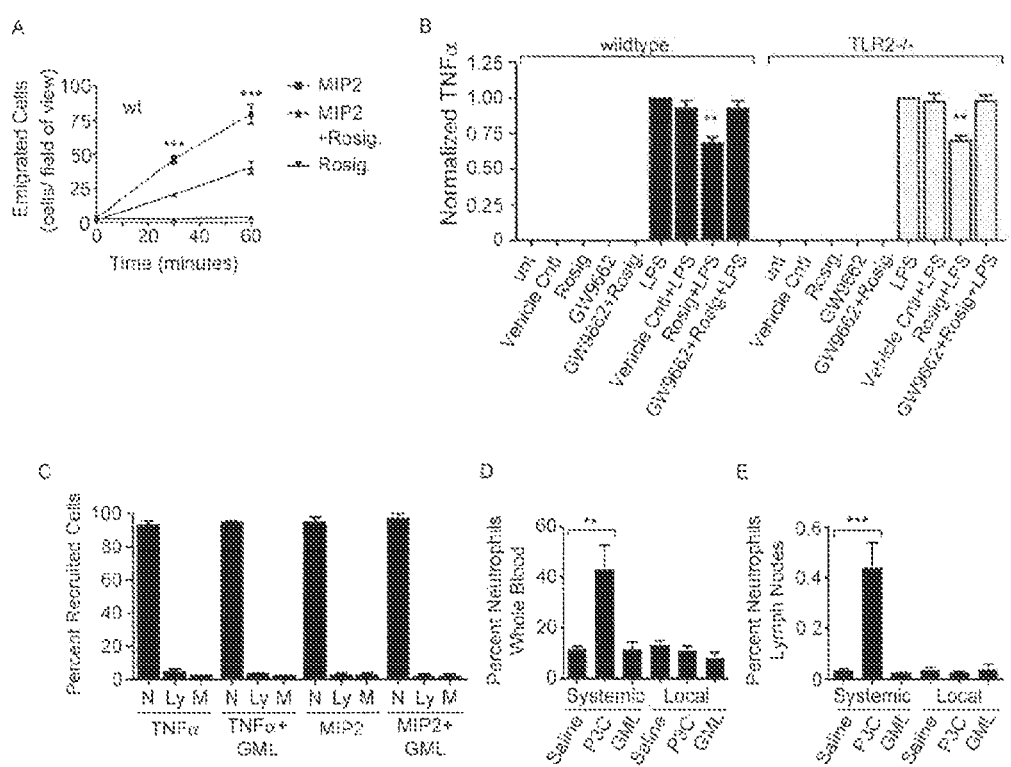
FIGS. 10A-E. PPARγ activation inhibits neutrophil recruitment in response to the chemokine MIP2.

Considering that the linoleate modification renders TLR2 ligands inhibitory, the inventors suspected that in the in vivo pro-inflammatory microenvironment, linoleate-derived linoleic acid could be modified in the presence of free radicals to form an oxo- or nitro-derivative, and thereby form a ligand for PPARγ (Villacorta et al., 2009). Therefore, the possibility that functional PPARγ signaling is involved in the inhibitory capacity of these ligands was examined. When mice were pretreated with GW9662, a specific PPARγ antagonist (Leesnitzer et al., 2002), LTA, GML and FSL1-Lin2 induced significantly more leukocyte recruitment than in the absence of PPARγ inhibition (FIG. 5A). As expected, in the case of LTA and GML the neutrophil emigration remained modest, as they have reduced activating potential. However, the emigration induced by FSL1-Lin2 in the presence of GW9662 was comparable to that observed in response to the parent FSL-1 compound. Clearly, inhibiting the anti-inflammatory capacity of these ligands by inhibiting PPARγ activation, allows the pro-inflammatory nature of these ligands to dominate in vivo. In line with these data, pretreatment with GW9662 or another PPARγ antagonist T0070907, abrogated the inhibitory effect of both LTA and GML towards neutrophil recruitment induced by TNFα and MIP2 (FIGS. 5B, 5C and 5D). In an additional experiment, the PPARγ agonist, Rosiglitazone, inhibited neutrophil recruitment to the same degree as GML when co-administered with MIP2 (FIG. 10A). The absence of TLR2 does not affect the capacity for PPARγ to become activated by Rosiglitazone (FIG. 10B). Finally, considering that hydroxy- or oxo-linoleic acid derivatives are the possible PPARγ ligands that initiate this inhibitory effect, and that the oxidation of linoleic acid in the inflamed in vivo environment is likely to occur in the presence of myeloperoxidase and $H_2O_2$ generated during a respiratory burst, the inventors assayed the inhibitory capacity of GML in a myeloperoxidase knockout (MPO–/–) background. Indeed Zhang et al. have shown that even in the presence of reactive oxygen species, the oxidation of lipids is not efficient in the absence of myeloperoxidase (Zhang et al., 2002). FIG. 5E demonstrates that the inhibitory capacity of GML is eliminated in the MPO–/– background. Recently it has been shown that systemic administration of the pro-inflammatory TLR2 ligand, Pam3CSK4 can cause leukocyte trafficking to the lymph nodes (McKimmie et al., 2009). In this model of acute inflammation, neutrophils are the predominate cells recruited into the tissue (FIG. 10C). The inventors evaluated the effect of systemic administration of Pam3CSK4 on neutrophils and found increased numbers of circulating blood neutrophils and increased, albeit low, numbers of neutrophils in the lymph nodes (FIG. 10D and FIG. 10E. Local administration of Pam3CSK4 does not cause any changes in neutrophil numbers in either the blood or the lymph nodes, (FIGS. 10D and 10E), although local administration of Pam3CSK4 causes significant neutrophil recruitment into the cremaster tissue (FIG. 6F). Most importantly, neither systemic nor local administration of GML altered neutrophil numbers in the blood or lymph nodes (FIGS. 10D and 10E). Therefore the functional consequences of host recognition of inhibitory TLR2 ligands are distinct from those of pro-inflammatory TLR2 ligands.

Figure 13:
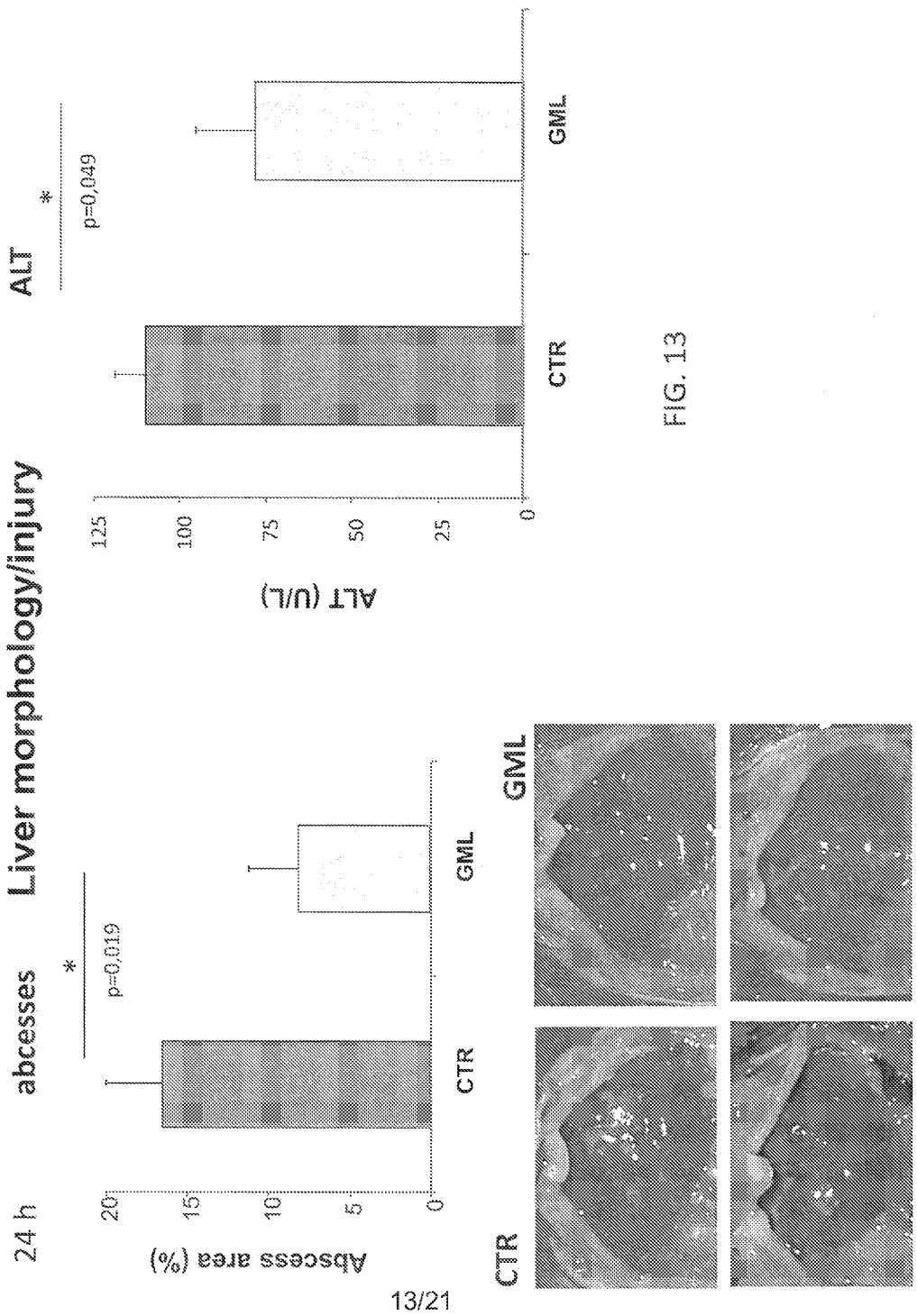
FIG. 13. Liver morphology from murine study shown in FIG. 12. Mice with S. aureus sepsis were euthanized after 24 hrs and their livers were removed and the areas of liver damage (abscess areas) were measured and analysed with ImageJ. Moreover, serum levels of alanine aminotransferase (ALT) were evaluated in blood obtained via cardiac puncture. Increased levels of ALT are indicative of hepatocellular injury. Groups of mice receiving GML versus control saline-treated animals are compared. Data are presented as mean±SEM.
Figure 14:
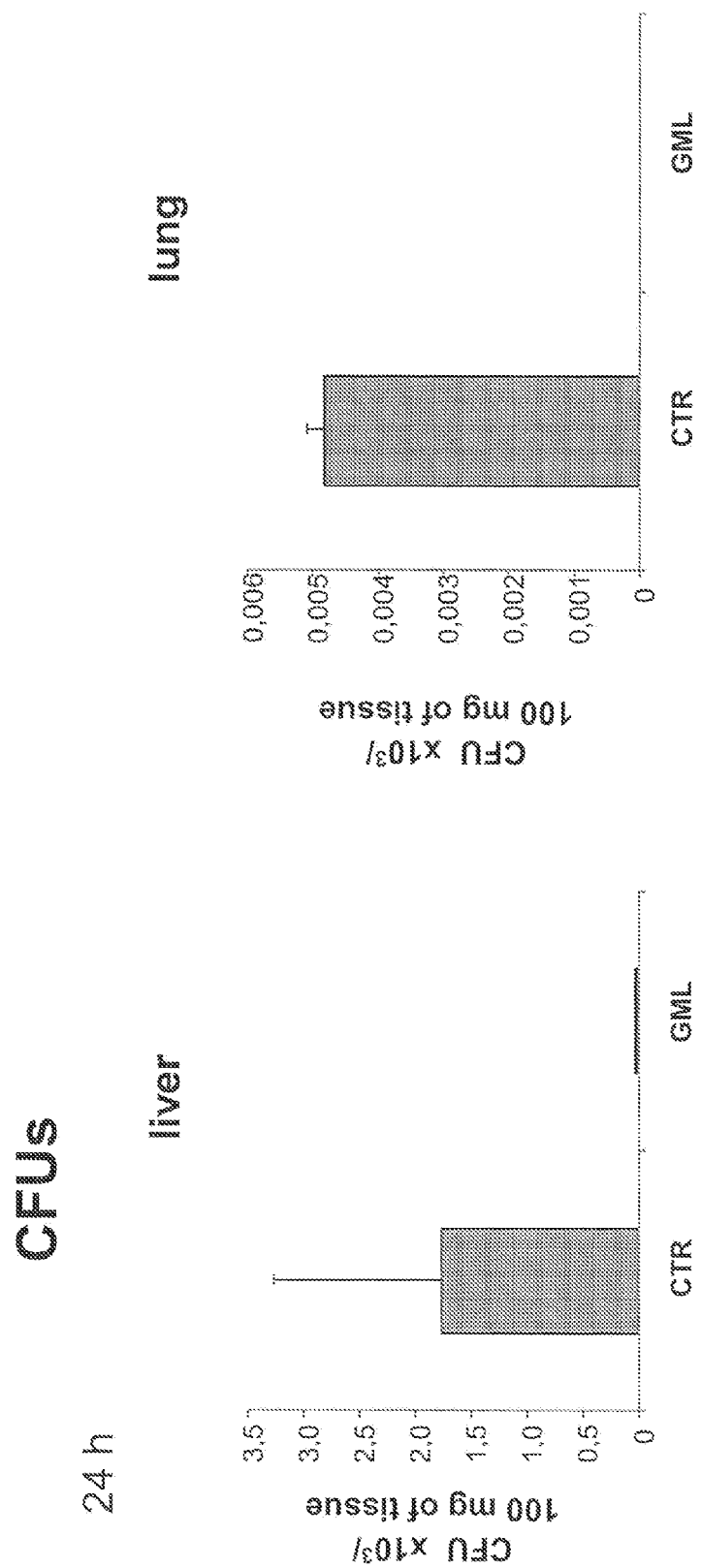
FIG. 14. Colony forming units (CFU) in liver and lung from murine study shown in FIG. 12. Mice with S. aureus sepsis were euthanized after 24 hrs and their livers and lungs were collected. They were subsequently homogenized, diluted and plated onto brain heart infusion (BHI) agar (37° C.). After overnight incubation the bacterial colonies (CFUs) were counted on the plates. Groups of mice receiving GML versus control saline-treated animals are compared. Data are presented as mean±SEM. No CFUs were found in blood of either group.
Figure 15:
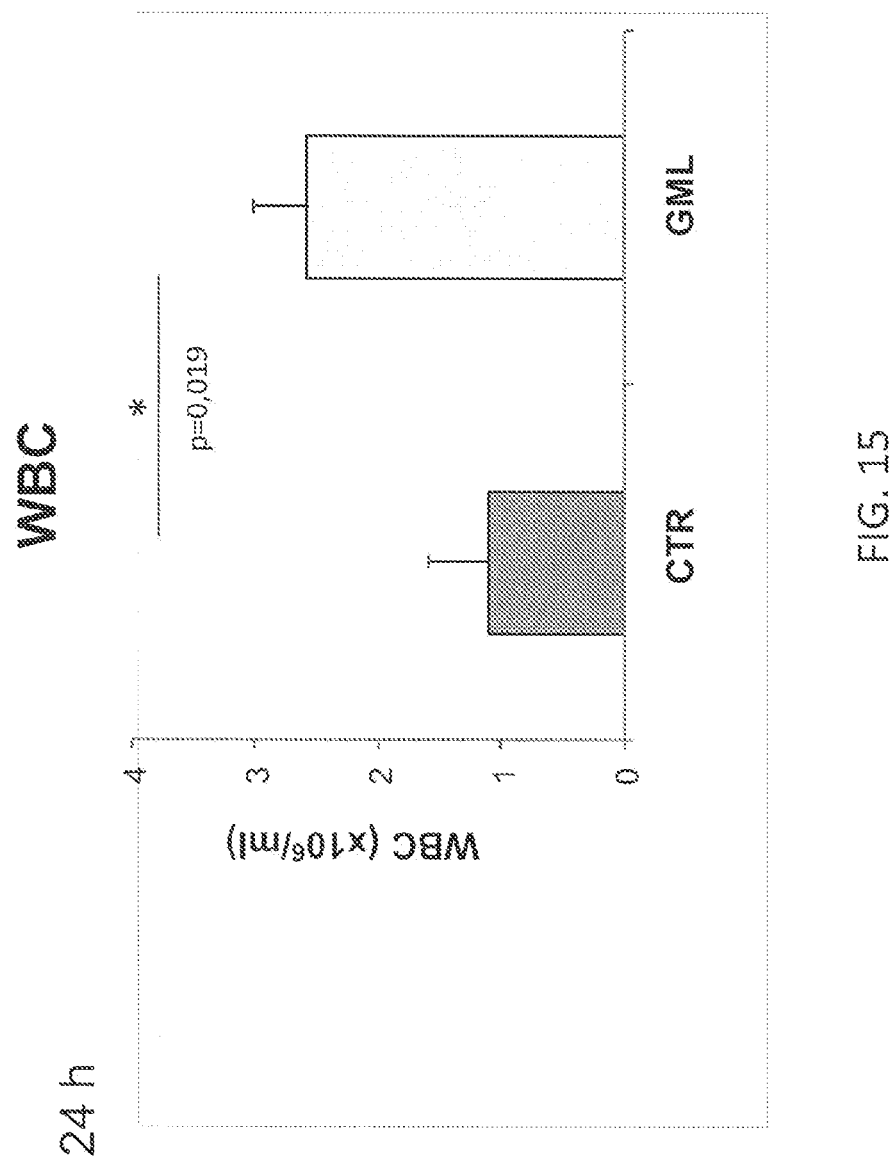
FIG. 15. White blood cell count (WBC) from murine study shown in FIG. 12. Blood obtained via cardiac puncture 24 hrs after S. aureus inoculation. White blood counts were counted with a hemocytometer following staining with Turk's solution (0.01% crystal violet in 3% acetic acid). Groups of mice receiving GML versus control saline-treated animals are compared. Data are presented as mean±SEM.
Figure 16:
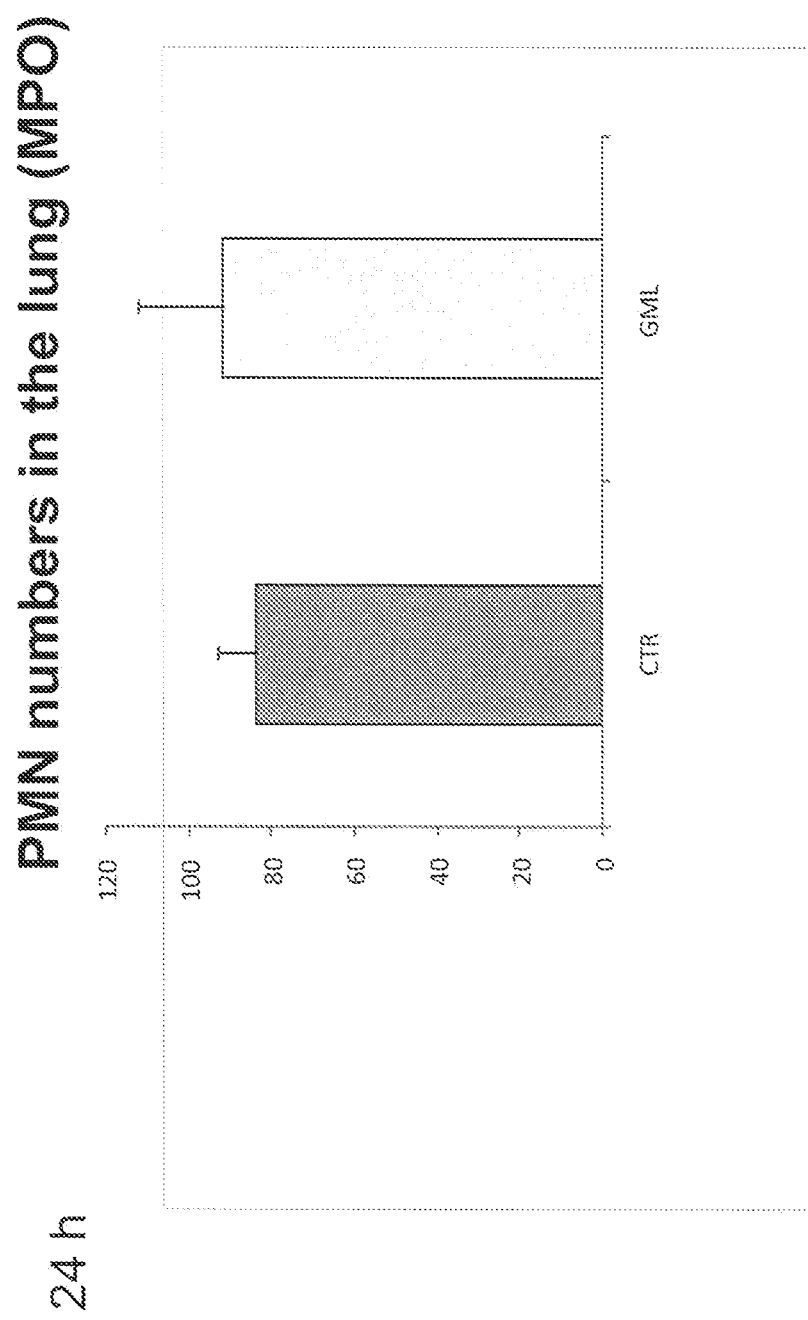
FIG. 16. Polymorphic neutrophil counts in lung tissue from murine study shown in FIG. 12. Levels of myeloperoxidase (MPO), an enzyme characteristic for neutrophils, were detected in lung homogenates. Lungs were collected from euthanized mice 24 hrs after S. aureus treatment. Increased levels of MPO are indicative of neutrophil accumulation and occurrence of inflammation. Groups of mice receiving GML versus control saline-treated animals are compared. Data are presented as mean±SEM.

FIGS. 12-19 all relate to an in vivo murine model of community-acquired MRSA sepsis (study design in FIG. 12). *S. aureus* epidemiology resides with its ability to rapidly acquire resistance to antibiotics and MRSA is currently the leading cause of community-associated bacterial infections. MRSA-associated systemic inflammation is characterized by multiple organ failure and high mortality ratio. The data here clearly show important effects of GML in *S. aureus* infection (see FIG. 19 for summary). Indeed, even though similar amounts of neutrophils are seen in organs (FIG. 16 the lung, FIG. 17 the liver), there are more leukocytes in the blood following GML administration, thereby allowing more neutrophils to get to infection sites (FIG. 15). Most importantly, however, GML significantly decreases liver injury as confirmed by two different tests. Namely, levels of alanine aminotransferase indicative of liver injury are lower, and abscess formation on the liver surface is significantly less severe (FIG. 13). In contrast, *S. aureus*-induced NET formation is stronger in animals treated with GML (FIG. 18) while concominantly, those mice are completely eradicated of *S. aureus* (FIG. 14) Neutrophil extracellular traps (NETs) are released by highly acitated neutrophils. Those structures are composed of DNA, histones and proteins originating from neutrophil granules, including proteases (e.g., neutrophil elastase, NE). Their function is to trap and kill bacteria. Thus, the stronger NET formation induced by GML might facilitate more efficient bacteria clearance. Overall, GML decreases inflammation-associated injury and bacteria spreading during *S. aureus* sepsis.

FIG. 20 shows the results from is a model of sterile inflammation. The middle row shows a dramatic decrease in neutrophil (light dots) recruitment to injured liver (dead cells are propidium iodide positive—diffuse grey areas in center) by GML, compared to CNTRL, which is quantified in the bottom panel.

Figure 21:
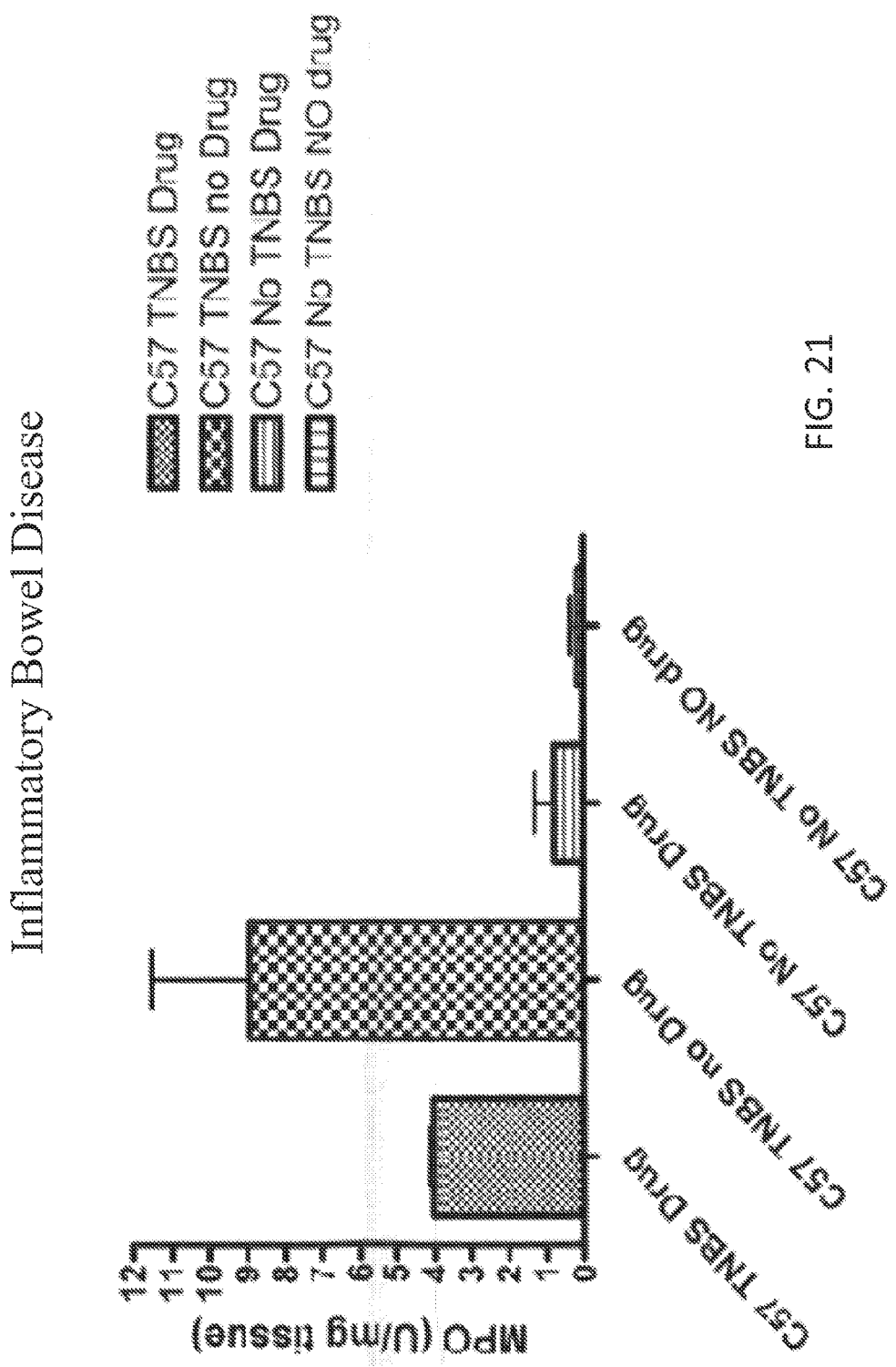
FIG. 21. Inflammatory bowel disease. IBD model in mice using TNBS which causes neutrophil influx and intestinal inflammation. Drug refers to GML and reduces neutrophil influx measured as MPO (bar A versus bar B).

The 2,4,6-trinitrobenzene sulfonic acid (TNBS)-induced murine colitis is an experimental model for human Inflammatory Bowel Disease (IBD). In this model, mice receive rectal administration of the contact sensitizing allergen TNBS in ethanol. Ethanol is included to break the mucosal barrier and allow penetration of TNBS into the bowel wall. TNBS was administered in the presence of absence of GML (5 mg), and 7 days later the bowel was excised and used to detect myloperoxidase, as a marker of neutrophil infiltration. A boosting dose of GML was given on day 3. In the presence of GML (Drug plus TNBS), the number of nutrophils present in the inflamed tissue was significantly less that the number of neutrophils in the bowel that did not receive GML (no drug plus TNBS) (FIG. 21). In the absence of TNBS, there was no neutrophil presence within the bowel, which was not affected by the presence of GML alone. (drug or no drug with no TNBS) (FIG. 21).

Example 3

Discussion

Historically, TLRs have been described as sentinel receptors that elicit pro-inflammatory responses when engaged by their cognate ligands (Beutler, 2009; Manicassamy and Pulendran, 2009); the inventors, however, describe a phenomenon where specific acylated TLR2 ligands inhibit the recruitment of neutrophils into an inflamed tissue in vivo. This inhibitory effect requires both TLR2 and the fatty acid and nuclear hormone receptor PPARγ, and not the major TLR2 signaling adaptor, MyD88. The inventors' data suggest that this phenomenon requires the functional involvement of PPARγ and that TLR2 may simply be required for internalization of the ligand. With regard to the structural requirements for a TLR2 ligand required for its anti-inflammatory properties, they found that modifications of the acyl chains and the peptide sequence of a lipopeptide TLR2 ligand can yield a TLR2 ligand with purely anti-inflammatory properties. Moreover, they show that the natural ligand, LTA, possesses these inhibitory characteristics. The exact molecular structure and the modification of the acyl chains required to derive a bona-fide PPARγ ligand, remains to be determined.

The inventors have provided no direct evidence that a MyD88-independent signaling pathway downstream of TLR2 is required for the anti-inflammatory response and thus TLR2 may serve to mediate a specific means of endocytosis that facilitates the delivery of anti-inflammatory ligands to their intracellular target, PPARγ. They suggest that the targeting of the lipopeptide GML, to GM1, alters its internalization in such a way as to mimic the internalization pathway of LTA. This internalization follows an alternative means of endocytosis from that observed with the 'classical' pro-inflammatory TLR2 ligands and effectively limits their pro-inflammatory potential (16, 27). Distinct spatial requirements for productive signaling is not a unique concept and in fact is consistent with TLR4 signaling where Mal/MyD88-driven responses proceed from the plasma membrane versus Tram/Trif signaling, which originates from complexes forming at the endosome. (Kagan et al., 2008). This would imply that the different classes of TLR2 ligands, pro-versus anti-inflammatory, utilize spatial and temporal separation of TLR2 receptor complexes to illicit distinct intracellular responses.

Although GML precisely mimics the inhibitory capacity of the LTA, linoleate may not be the inhibitory component within the LTA. Ultimately, the acyl chains of any naturally produced TLR2 ligand would, in part, reflect the fatty acid constituents of the bacterial membranes. Although bacteria typically synthesize only monounsaturated fatty acids, the fatty acid composition of bacteria is markedly affected by the growth conditions (O'Leary, 1962). Unsaturated fatty acids in the media would be incorporated into the bacterial membranes and could then form part of the bacterial lipoproteins (Tibor et al., 1999) thus the microbial environment could profoundly influence the production of any anti-inflammatory TLR2 ligands. Nevertheless, it is clear that the inhibitory effect of LTA depends on PPARγ activation, similar to the synthetic inhibitory TLR2 ligand, GML.

These data define a model where a subclass of TLR2 ligands can be considered to have both pro- and anti-inflammatory properties through the functional use of two receptors, namely TLR2 and PPARγ. The preponderance for one biologic effect over the other is related to the specific structural composition of each TLR2 ligand. The data we present herein fundamentally changes the inventors' conceptual understanding of how bacterial-derived TLR2 ligands can influence neutrophil responses and as such host-microbial interactions. The inventors have provided a mechanistic understanding of how this can occur through the synthesis of a TLR2 ligand with purely anti-inflammatory properties. It is possible that there may be other naturally-occurring inhibitory TLR2 ligands, besides LTA, and that these ligands may profoundly influence host-pathogen interactions as well as normal interactions with the microbiome. Furthermore, the synthetic ligand described herein, GML, may prove to have therapeutic value in pathological settings where neutrophil recruitment is associated with disease.

The in vivo data clearly show important effects of GML in *S. aureus* infection (see FIG. 19 for summary). *S. aureus* infection causes profound liver and lung damage and in patients causes significant morbidity and mortality. The inventors believe much of this may be due to inappropriate inflammation and misdirection of neutrophils, GML may be lowering some of the inappropriate inflammation while allowing the immune system to not be distracted and focus on killing *S. aureus*. Indeed, even though similar amounts of neutrophils are seen in organs, there are more neutrophils in the blood following GML administration, thereby allowing more neutrophils to get to infection sites. The data clearly show less infection in multiple organs (in fact complete eradication of S. aureus) resulting in less liver injury. However, it remains unclear exactly why there is less damage to the liver at neutrophil numbers do not seem to be changed. Also, the effect does not seem to be dependent neutrophil extracellular traps.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. References

The following references, to the extent that they provide exemplary procedural or other details supplementary to those set forth herein, are specifically incorporated herein by reference.

Akira, Biochem. Soc. Transactions, 28: 551-556, 2000.
Aravalli et al., J. Neuroinflammation, 5:30, 2008.
Arbibe et al., Nat. Immunol., 1(6):533-540, 2000.
Ariza et al., J. Immunol., 182:851-859, 2009.
Asai et al., J. Medical Microbiol., 56:459-465, 2007.
Beutler, Blood. 113:1399-1407, 2009.
Brikos and O'Neill, In: Handbook of experimental pharmacology, 21-50, 2008.
Brown and Mayer, Amer. J. Gastroenter., 102:2058-2069, 2007.
Burke et al., J. Immunol., 179:3222-3230, 2007.
Buwitt-Beckmann et al., J. Biol. Chem., 281:9049-9057, 2006.
Cario et al., J. Immunol., 164(2):966-972, 2000.
Carvalho-Tavares et al., Circulation Res., 87:1141-1148, 2000.
Casadevall et al., Infection Immunity, 67(8):3703-3713, 1999.
Chang et al., J Leukocyte Biol., 82:479-487, 2007.
Chaudhary et al., Blood, 91(11):4020-4027, 1998.
Debierre-Grockiego et al., J Immunol., 179:1129-1137, 2007.
Deininger et al., Clin. Vaccine Immunol., 14:1629-1633, 2007.
Du et al., Eur. Cytokine Netw., 11(3):362-371, 2000.
Eldon, Development, 120(4):885-899, 1994.
Georgel et al., Infection Immunity, 73:4512-4521, 2005.
Heumann et al., Curr. Opin. Microbiol., 1(1):49-55, 1998.
Huang et al., J. Immunol., 182:4965-4973, 2009.
Jaeschke and Hasegawa, Liver Int., 26:912-919, 2006.
Janeway, Immunol. Today, 13(1):11-16, 1992.
Jiang et al., Nature Med., 11:1173-1179, 2005.
Jiang et al., Nature, 391:82-86, 1998.
Jin et al., Cell, 130:1071-1082, 2007.
Kadowaki et al., J. Exp. Med., 194(6):863-869, 2001.
Kagan et al., Nat. Immunol., 9(4):361-368. 2008
Kang et al., Immunity, 31:873-884, 2009.
Kawakami et al., Circul. Res., 103:1402-1409, 2008.
Kerfoot and Kubes, J. Leukocyte Biol., 77:862-867, 2005.
Krishnegowda et al., J. Biol. Chem., 280:8606-8616, 2005.
Kurokawa et al., et al., J. Biol. Chem., 284:8406-8411, 2009.
Leesnitzer et al., Biochemistry, 41:6640-6650, 2002.
Ley et al., Nature Rev., 7:678-689, 2007.
Li et al., Exp. Dermatol., 18(7):603-610, 2009.
Liang et al., J. Immunol., 182:2978-2985, 2009.
Long et al., PloS One, 4:e5601, 2009.
Manicassamy and Pulendran, Seminars Immunol., 21:185-193, 2009.
Massari et al., J. Immunol., 176:2373-2380, 2006.
Matsubara et al., FEBS Lett., 456:253-256, 1999.
McKimmie et al., Blood, 113:4224-4231, 2009.
Means et al., J. Immunol., 163:6748-6755, 1999.
Means et al., Life Sci., 68(3):241-258 2000.
Medzhitov et al., Mol. Cell, 2(2):253-258, 1998.
Medzhitov et al., Nature, 388(6640):394-397, 1997.
Morath et al., Infection Immunity, 70:938-944, 2002.
Morath et al., J. Experim. Med., 193:393-397, 2001.
Nilsen et al., J. Leukocyte Biol., 84:280-291, 2008.
O'Neill, Biochem. Soc. Trans., 28(5):557-563, 2000.
O'Leary, Bacteriological Rev., 26:421-447, 1962.
Ozinsky et al., Proc. Natl. Acad. Sci. USA, 97:13766-13771, 2000.
Pecora et al., J. Immunol., 177:422-429, 2006.
Petri et al., J. Immunol., 180:6439-6446, 2008.
Poltorak et al., Blood Cells Mol Dis., 24(3):340-355, 1998.
Reddy et al., Blood, 112:4250-4258, 2008.
Remington's Pharmaceutical Sciences, 15th Ed., 33:624-652, 1990.
Sato et al., J. Immunol., 171:417-425, 2003.
Schaefer et al., J. Clinical Invest., 115:2223-2233, 2005.
Schroder et al., J. Biol. Chem., 278:15587-15594, 2003.
Serhan et al., Nature Rev., 8:349-361, 2008.
Stein et al., Cell, 65(5):725-735, 1991.
Straus and Glass, Trends Immunol., 28:551-558, 2007.
Takeuchi et al., Gene, 231(1-2):59-65, 1999.
Tarrago-Trani and Storrie, Advanced Drug Del. Rev., 59:782-797, 2007.
Termeer et al., J. Experimental Med., 195:99-111, 2002.
Tibor et al., Infection Immunity, 67:4960-4962, 1999.
Underhill, J. Endotoxin Res., 9:176-180, 2003.
Villacorta et al., Clin. Sci. (Loud), 116:205-218, 2009.
Watanabe et al., J. Am. Oil Chem. Soc., 71:325-330, 1994.
Yamamoto et al., Science NY, 301:640-643, 2003.
Yang et al., J. Immunol., 163(2):639-643, 1999.
Yipp et al., J. Immunol., 168:4650-4658, 2002.
Zahringer et al., Immunobiology, 213:205-224, 2008.
Zemans et al., Amer. J. Respiratory Cell Molecul. Biol., 40:519-535, 2009.
Zhang et al., Blood, 99:1802-1810, 2002.

The invention claimed is:

1. A method of inhibiting pro-inflammatory signaling in a subject in need thereof or of inhibiting leukocyte recruitment to an inflammatory site in a subject in need thereof comprising administering to said subject a modified Toll-Like Receptor 2 (TLR2) ligand comprising (a) a fatty acid di- or tri-linoleate and (b) a monosialotetrahexosylganglioside (GM1)-binding peptide wherein said GM1-binding peptide comprising the peptide sequence of VWRLLAPPFSNRLLP (SEQ ID NO: 1), WRLLAPPFSNRLLP (SEQ ID NO: 2) or (W/F)RXL(X/P)(P/X)XFXX(R/X)(X/R)XP (SEQ ID NO: 3), where X can be any amino acid.

2. The method of claim 1, wherein said TLR2 ligand is a di-linoleate compound.

3. The method of claim 1, wherein said TLR2 ligand is a tri-linoleate compound.

4. The method of claim 1, wherein said subject is a human.

5. The method of claim 1, wherein said subject is a non-human mammal.

6. The method of claim 1, wherein said di- or tri-linoleate is a peroxisome proliferation activated receptor (PPAR) ligand.

7. The method of claim 1, wherein said subject suffers from chronic inflammation.

8. The method of claim 7, wherein said chronic inflammation comprises leukyocyte recruitment.

9. The method of claim 7, wherein chronic inflammation includes inflammatory bowel disease, arthritis, psoriasis, respiratory neutrophila, chronic tissue injury.

10. The method of claim 1, wherein said subject suffers from acute inflammation.

11. The method of claim 10, wherein acute inflammation comprises tissue trauma, sepsis, methicillin-resistant *Staphylococcus* infection, sterile injury, acute inflammatory tissue, injury respiratory neutrophilia, acute neutrophilic dermatosis, and during organ/tissue transplantation.

12. The method of claim 1, wherein said TLR2 ligand is administered subcutaneously, topically, intravenously, suppository, or via a shunt.

13. The method of claim 1, further comprising administering to said subject a second anti-inflammatory therapy.

14. The method of claim 13, said second anti-inflammatory therapy comprises an NSAID, a steroid, an anti-adhesion molecule therapy, a COX inhibitor, an immunomodulator, an anti-histamine, an antibiotic or an anti-viral.

15. The method of claim 1, wherein leukyocyte recruitment to a site is reduced 10%, 20%, 30%, 40%, 50%, 60% or 75% as compared to untreated control.

16. A modified lipopeptide Toll-Like Receptor 2 (TLR2) ligand comprising (a) a fatty acid di- or tri-linoleate and (b) a monosialotetrahexosvlganglioside (GM1)-binding peptide wherein said GM1-binding peptide comprising the peptide sequence of VWRLLAPPFSNRLLP (SEQ ID NO: 1), WRLLAPPFSNRLLP (SEQ ID NO: 2) or (W/F)RXL(X/P)(P/X)XFXX(R/X)(X/R)XP (SEQ ID NO: 3), where X can be any amino acid.

17. The lipopeptide of claim 16, wherein said fatty acid di- or tri-linoleate activates PPARγ.

\* \* \* \* \*

SEQUENCE LISTING

<160> NUMBER OF SEQ ID NOS: 3

<210> SEQ ID NO 1
<211> LENGTH: 15
<212> TYPE: PRT

```
<213> ORGANISM: Artificial Sequence
<220> FEATURE:
<223> OTHER INFORMATION: Synthetic peptide

<400> SEQUENCE: 1

Val Trp Arg Leu Leu Ala Pro Pro Phe Ser Asn Arg Leu Leu Pro
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Trp Arg Leu Leu Ala Pro Pro Phe Ser Asn Arg Leu Leu Pro
1               5                   10

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 3

Trp Phe Arg Xaa Leu Xaa Pro Pro Xaa Xaa Phe Xaa Xaa Arg Xaa Xaa
1               5                   10                  15

Arg Xaa Pro
```